(12) United States Patent
Suzuki et al.

(10) Patent No.: US 11,242,446 B2
(45) Date of Patent: Feb. 8, 2022

(54) CELLULOSE COMPOSITE

(71) Applicant: ASAHI KASEI KABUSHIKI KAISHA, Tokyo (JP)

(72) Inventors: Ryo Suzuki, Tokyo (JP); Koichiro Enatsu, Tokyo (JP); Naoaki Yamasaki, Tokyo (JP)

(73) Assignee: ASAHI KASEI KABUSHIKI KAISHA, Tokyo (JP)

( * ) Notice: Subject to any disclaimer, the term of this patent is extended or adjusted under 35 U.S.C. 154(b) by 270 days.

(21) Appl. No.: 15/566,075

(22) PCT Filed: Apr. 13, 2015

(86) PCT No.: PCT/JP2015/061364
§ 371 (c)(1),
(2) Date: Oct. 12, 2017

(87) PCT Pub. No.: WO2016/166798
PCT Pub. Date: Oct. 20, 2016

(65) Prior Publication Data
US 2018/0134878 A1 May 17, 2018

(51) Int. Cl.
| | | |
|---|---|---|
| *A23F 5/14* | (2006.01) |
| *C08L 1/28* | (2006.01) |
| *A61K 47/36* | (2006.01) |
| *A61K 47/38* | (2006.01) |
| *C08L 5/04* | (2006.01) |
| *C08L 1/00* | (2006.01) |
| *C08B 1/00* | (2006.01) |
| *C08L 3/04* | (2006.01) |
| *A23L 2/52* | (2006.01) |
| *A23L 33/24* | (2016.01) |
| *A23L 29/262* | (2016.01) |
| *A23L 33/105* | (2016.01) |
| *A61K 9/10* | (2006.01) |

(52) U.S. Cl.
CPC .............. *C08L 1/286* (2013.01); *A23F 5/14* (2013.01); *A23L 2/52* (2013.01); *A23L 29/262* (2016.08); *A23L 33/105* (2016.08); *A23L 33/24* (2016.08); *A61K 9/10* (2013.01); *A61K 47/36* (2013.01); *A61K 47/38* (2013.01); *C08B 1/00* (2013.01); *C08L 1/00* (2013.01); *C08L 3/04* (2013.01); *C08L 5/04* (2013.01); *A23V 2002/00* (2013.01); *C08L 2203/02* (2013.01); *C08L 2205/025* (2013.01); *C08L 2205/03* (2013.01)

(58) Field of Classification Search
CPC ......... A23V 2002/00; C08L 1/00; C08L 1/04; C08L 1/02; C08L 1/28; C08L 1/286; C08L 1/32; C08L 2205/03; C08L 2205/025; C08L 2203/02; C08L 5/00; C08L 5/04; C08L 3/04; A23L 33/105; A23L 33/24; A23L 29/262; A23L 29/00; A61K 47/36; A61K 47/38; A61K 9/10; C08B 1/00; A23F 5/14
See application file for complete search history.

(56) References Cited

U.S. PATENT DOCUMENTS

| | | | | |
|---|---|---|---|---|
| 5,366,742 A | * | 11/1994 | Tuason, Jr. | .......... A23C 9/1544 |
| | | | | 426/573 |
| 2013/0022730 A1 | * | 1/2013 | Obata | ....................... A23L 2/02 |
| | | | | 426/590 |
| 2014/0171521 A1 | * | 6/2014 | Enatsu | ...................... A23L 2/02 |
| | | | | 514/781 |

FOREIGN PATENT DOCUMENTS

| | | | |
|---|---|---|---|
| JP | S40012174 | | 6/1965 |
| JP | 2006508195 A | | 3/2006 |
| JP | WO2011/125742 | * | 10/2011 |
| JP | 2013040228 A | | 2/2013 |
| JP | WO2013/022090 | * | 2/2013 |
| JP | 2013118819 A | | 6/2013 |
| JP | 2013226103 A | | 11/2013 |
| JP | 2014087313 A | | 5/2014 |
| JP | 2015074736 A | | 4/2015 |
| KR | 1020120022012 A | | 9/2012 |
| WO | 2011125742 A1 | | 10/2011 |
| WO | 2013022090 A1 | | 2/2013 |
| WO | 2013122127 A1 | | 8/2013 |

OTHER PUBLICATIONS

International Search Report from Application No. PCT/JP2015/061364, dated Jun. 16, 2015.
International Preliminary Report on Patentability from Application No. PCT/JP2015/061364, dated May 19, 2015.
Supplemental European Search Report issued in EP 15 88 9136.6, dated Oct. 2, 2018.

* cited by examiner

Primary Examiner — Smita S Patel
(74) Attorney, Agent, or Firm — Greenblum & Bernstein, P.L.C.

(57) ABSTRACT

[Problem] The present invention addresses the problem of providing a cellulose composite whereby the cellulose composite itself disperses stably even when ions are blended in a high concentration in a beverage, and also has excellent suspension stability.

[Solution] A cellulose composite comprising cellulose, an anionic polysaccharide not having a chemically crosslinked structure, and water-absorbent particles comprising a compound having a chemically crosslinked structure wherein the cellulose composite has a viscosity of 10 mPa·s or higher when 1 mass % of the cellulose composite is dispersed in an aqueous solution in which 0.45 g of sodium bicarbonate is dissolved in 100 mL of pure water.

9 Claims, No Drawings

CELLULOSE COMPOSITE

TECHNICAL FIELD

The present invention relates to a cellulose composite.

BACKGROUND ART

Cellulose composites constructed from cellulose and an anionic polysaccharide are known to form a cellulose colloid in an aqueous medium and to present good suspension stability. Such cellulose composites are widely used in fields such as foods, pharmaceuticals, cosmetics, paints, ceramics, resins, catalysts, and other industrial products. Such cellulose composites are used in particular in suspension stabilizers, emulsion stabilizers, thickener stabilizers, and other such stabilizers, texture-imparting agents, cloudy agents, whiteness improvement, fluidity modification, abrasives, dietary fiber, fat/oil substitution, and the like. For example, such cellulose composites are added for suspension stability of high specific-gravity, water-insoluble components such as milk calcium and calcium carbonate in calcium-fortified milk, which is a beverage.

Various studies have been conducted up to now on using these cellulose composites to improve suspension stability in media where minerals, that is, ions, are present in only small amounts.

Patent Reference 1 discloses a water-dispersible composite containing microcellulose and carboxymethyl cellulose sodium.

Patent Reference 2 discloses a cellulose composite comprising cellulose and a polysaccharide. This cellulose composite is described as containing colloidal cellulose composites, with the median diameter of the colloidal cellulose composites measured by dynamic light scattering being 0.85 μm or greater. In addition, carboxymethyl cellulose sodium is described as being preferred as the polysaccharide. Furthermore, this reference describes a method for producing a cellulose composite using a solids fraction of 35 mass % or higher and a temperature of 80° C. or lower in a wet co-processing step of a mixture comprising cellulose, polysaccharide, and an aqueous medium. And, a water-dispersible composition using the cellulose composite is described as having excellent suspension stability in beverages blended with a high concentration of cocoa, coffee extract, and the like.

Patent Reference 3 discloses a water-dispersible composition obtained by adding any inorganic salt that is substantially completely soluble in water as an anti-slip agent in addition to microcellulose and a hydrocolloid containing carrageenan or alginate, and kneading at high shear force. Calcium chloride is described as being especially preferred as the inorganic salt. In addition, this water-dispersible composition is described as having excellent suspension stability in chocolate beverages and drinkable yoghurt products.

PRIOR ART REFERENCES

Patent References

Patent Reference 1: Japanese Examined Patent Application Publication No. S40-12174
Patent Reference 2: International Publication No. WO2013/022090 pamphlet
Patent Reference 3: Japanese Unexamined Patent Application Publication No. 2006-508195

SUMMARY OF THE INVENTION

Problems to be Solved by the Invention

In association with an increase in patients with heat stroke in recent years due to global warming, products have been developed that blend minerals as typified by sodium into cocoa, coffee, black tea, or other such flavored beverages in cans or PET containers. Since the minerals are present in an ionic state in the beverage in such products, the stabilizer added to the beverage becomes unstable when the mineral concentration becomes high, leading to a problem in that the stabilizer itself precipitates. And, when the stabilizer itself precipitates, water-insoluble components such as proteins and the like also tend to precipitate. A cellulose composite that allows the stabilizer itself to maintain a dispersed state stably even in a beverage in which a high concentration of minerals is blended and actualizes a suspension stabilizing effect on the other water-insoluble components in the beverage is therefore desired.

The above problems were not solved adequately by conventional cellulose composites constructed from cellulose and an anionic polysaccharide. In sum, the cellulose composites aggregated with each other and precipitated, losing dispersion stability, and did not satisfactorily actualize their function as a stabilizer in beverages blended with a high concentration of minerals, that is, ions, even when conventional cellulose composites were used.

For example, if we look at the cellulose composite or water-dispersible composition described in Patent References 1 and 2, the dispersion stability of the cellulose itself is good. Moreover, when the cellulose composite described in Patent Reference 2 is used, adequate suspension stability is obtained even in rich-tasting beverages blended with a high concentration of cocoa, coffee extract, black tea extract, or the like. However, the problem is that when a high concentration of ions is blended into the beverage, the cellulose composites aggregate with each other and precipitate, losing dispersion stability, and do not satisfactorily actualize their function as a stabilizer.

The cellulose composite described in Patent Reference 3 has dispersion stability that makes it possible for the composite itself to disperse stably even when a high concentration of ions is blended into the beverage. However, the suspension stabilizing effect on other water-insoluble components in the beverage is inadequate, and the problem is still that the composite precipitates and aggregates in beverages blended with a high concentration of ions.

The present invention addresses the problem of providing a cellulose composite that itself has dispersion stability as well as excellent suspension stability even in a system in which a high concentration of ions is present.

Means Used to Solve the Problems

In the first aspect of the present invention, the present inventors discovered that when water-absorbent particles are added to cellulose and an anionic polysaccharide to make a highly composited cellulose composite, the cellulose composite itself has dispersion stability as well as excellent suspension stability even in beverages of high ionic strength, and thereby achieved the present invention. "Compositing" in the present invention means that at least part of the cellulose surface is covered by an anionic polysaccharide by chemical bonding such as hydrogen bonding or the like. A "composite" of cellulose means that at least part of the cellulose surface is covered by an anionic polysaccharide by chemical bonding such as hydrogen bonding or the like.

Ionic strength in this specification also means the strength presented by one ion or the sum of multiple ions in an electrolyte solution. The ionic strength is calculated by adding all of the products of the molar concentration mi and the value obtained by squaring the charge Zi of each ion and further dividing by 2. Specifically, the ionic strength is defined by the following formula:

$$0.5 \times \Sigma mi(Zi)^2$$

For example, the ionic strength of a 0.1 M $MgSO_4$ aqueous solution is calculated as $0.5 \times (0.1 \times 2^2 + 0.1 \times (-2)^2) = 0.4$ in accordance with the above formula.

In addition, "dispersion stability" in this specification means the dispersion stability of the cellulose composite itself when the cellulose composite is dispersed in an aqueous medium free of water-insoluble components. Specifically, it means that the cellulose particles do not separate, aggregate, precipitate, or the like and exhibit a uniform appearance.

Also, "suspension stability" in this specification means that water-insoluble components are suspension stabilized by the effect of addition of the cellulose composite when water-insoluble components other than the cellulose composite, such as cocoa powder or calcium, functional food materials, or the like, are included. Specifically, it means that particles of not only cellulose, but water-insoluble components do not separate, aggregate, precipitate, or the like, and exhibit a uniform appearance.

In a further explanation of the first aspect of the present invention, it was discovered that, due to the presence of water-absorbent particles in the cellulose composite, the water-absorbent particles themselves swell when the cellulose composite containing the water-absorbent particles is dispersed in an aqueous medium, promoting breakdown from the interior of the cellulose composite particles and as a result improving the dispersibility of the cellulose composite. Therefore, the cellulose composite of the present invention can be produced by a method that comprises a step of compositing cellulose, an anionic polysaccharide not having a chemically crosslinked structure, and water-absorbent particles comprising a compound having a chemically crosslinked structure.

The second aspect of the present invention relates to a method that makes it possible to composite an anionic polysaccharide more highly with cellulose. Specifically, the present inventors discovered that it becomes possible to knead by high kneading energy in a semisolid state in which the viscosity of the kneaded product is high by effectively raising the solids fraction proportion (meaning the percentage of the dry mass of the kneaded product relative to the mass of the kneaded product) during kneading by causing the water contained in the cellulose to be absorbed by the particles by adding water-absorbent particles when kneading cellulose and an anionic polysaccharide. As a result, it was discovered that it becomes possible to composite an anionic polysaccharide having a protective colloid property such as carboxymethyl cellulose sodium more highly with cellulose, that the cellulose composite itself disperses stably even in beverages with improved ionic resistance of the composite and high ionic strength, and that a cellulose composite having excellent suspension stability can be obtained. Furthermore, "protective colloid property" here means that the colloidal cellulose surface is covered by anionic polysaccharide to suppress neutralization of the charge of the cellulose particle surface by outside ions.

Specifically, the present invention is as follows.

(1) A cellulose composite comprising cellulose, an anionic polysaccharide not having a chemically crosslinked structure, and water-absorbent particles comprising a compound having a chemically crosslinked structure, wherein the cellulose composite has a viscosity of 10 mPa·s or higher when 1 mass % of the cellulose composite is dispersed in an aqueous solution in which 0.45 g of sodium bicarbonate is dissolved in 100 mL of pure water.

(2) The cellulose composite of (1) above wherein the water-absorbent particles have a saturated water absorption of 3 mL/g or higher.

(3) The cellulose composite of (1) or (2) above wherein an amount of the water-absorbent particles contained is 0.5-15 mass %.

(4) The cellulose composite of any of (1)-(3) above wherein the compound having a chemically crosslinked structure is selected from the group consisting of carboxymethyl cellulose calcium, hydroxyphosphoric acid-crosslinked starch, croscarmellose sodium, and calcium alginate.

(5) The cellulose composite of any of (1)-(4) above wherein the compound having a chemically crosslinked structure is carboxymethyl cellulose calcium.

(6) The cellulose composite of any of (1)-(5) above wherein the anionic polysaccharide not having a chemically crosslinked structure is selected from the group consisting of carboxymethyl cellulose sodium and xanthan gum.

(7) The cellulose composite of any of (1)-(6) above wherein the polysaccharide not having a chemically crosslinked structure is carboxymethyl cellulose sodium.

(8) The cellulose composite of any of (1)-(7) above wherein a blend ratio of the cellulose/the anionic polysaccharide not having a chemically crosslinked structure is 50-99 parts by mass/1-50 parts by mass.

(9) A method for producing the cellulose composite of any of (1)-(8) above comprising a step of compositing the cellulose, the anionic polysaccharide not having a chemically crosslinked structure, and the water-absorbent particles comprising a compound having a chemically crosslinked structure.

(10) A method for producing a cellulose composite comprising cellulose and an anionic polysaccharide not having a chemically crosslinked structure wherein the method comprises a step of compositing the cellulose and the anionic polysaccharide not having a chemically crosslinked structure in the presence of water-absorbent particles comprising a compound having a chemically crosslinked structure.

(11) A food comprising the cellulose composite of any of (1)-(8) above.

(12) An industrial product comprising the cellulose composite of any of (1)-(8) above.

(13) A pharmaceutical comprising the cellulose composite of any of (1)-(8) above.

(14) A coffee beverage comprising the cellulose composite of any of (1)-(8) above.

Advantages of the Invention

The present invention makes it possible to provide a cellulose composite having dispersion stability even in a system in which minerals, that is, ions, are present in a high concentration, as well as excellent suspension stability.

Mode for Carrying Out the Invention

The present invention is described concretely below.

The cellulose composite of the present invention is a cellulose composite comprising cellulose, an anionic polysaccharide not having a chemically crosslinked structure, and water-absorbent particles comprising a compound having a chemically crosslinked structure wherein the viscosity is 10 mPa·s or higher when 1 mass % of the cellulose composite is dispersed in an aqueous solution in which 0.45 g of sodium bicarbonate is dissolved in 100 mL of pure water.

<Cellulose>

"Cellulose" in the present invention is a type of β-glucan having a structure in which glucose is polymerized by β bonds. Examples of the raw material include fibrous celluloses such as wood, bamboo, wheat straw, rice straw, cotton, ramie, bagasse, kenaf, beet, sea squirt, and bacterial cellulose. The fibrous cellulose may also include components other than cellulose such as hemicellulose, lignin, and the like. One type of fibrous cellulose among these can be used as the raw material, or a mixture of two or more types can be used.

<Average Degree of Polymerization of Cellulose>

The cellulose used in the present invention is preferably microcrystalline cellulose, and microcrystalline cellulose having an average degree of polymerization of 500 or less is especially preferred. The average degree of polymerization can be measured by the reduced specific viscosity method by copper ethylenediamine solution described in the "14$^{th}$ Revised Japan Pharmacopoeia," (published by Hirokawa Shoten) microcrystalline cellulose identification test (3). An average degree of polymerization of 500 or less is preferred because physical treatments such as stirring, pulverization, and grinding of the cellulosic material in the step that composites it with an anionic polysaccharide are facilitated, and the advance of compositing becomes easier. The average degree of polymerization is more preferably 300 or less, even more preferably 250 or less. Since a lower average degree of polymerization facilitates the control of compositing, the lower limit is not particularly restricted, but the preferred range is 10 or above.

<Hydrolysis of Cellulose>

Examples of the method of controlling the average degree of polymerization include hydrolysis of the fibrous cellulose. Due to hydrolysis, depolymerization of the amorphous cellulose in the interior of the fibrous cellulose progresses, and the average degree of polymerization becomes lower. Since hydrolysis simultaneously also removes impurities such as hemicellulose and lignin in addition to the above amorphous cellulose, the interior of the fibrous cellulose becomes porous. This facilitates mechanical treatment of the cellulose and makes it easier to make the cellulose finer in the step that applies mechanical shear force to the cellulose and anionic polysaccharide as the kneading step. As a result, the surface area of the cellulose increases, and control of compositing with the anionic polysaccharide is facilitated.

The method of hydrolysis is not particularly restricted; examples include acid hydrolysis, hot water decomposition, steam explosion, microwave decomposition, and the like. These methods may be used individually or in a combination of two or more types. In acid hydrolysis, the average degree of polymerization can be controlled easily by adding a suitable amount of a protic acid, carboxylic acid, Lewis acid, heteropoly acid, or the like to the fibrous cellulose which is dispersed in an aqueous medium, and heating while stirring. The reaction conditions such as the temperature, pressure, time, and the like in this instance differ depending on the type of cellulose, cellulose concentration, type of acid, and acid concentration, but are adjusted as is appropriate for attaining the target average degree of polymerization. An example is conditions comprising using a 2 mass % or less mineral acid aqueous solution and treating the cellulose for 10 minutes or longer at 100° C. or higher under increased pressure. Under these conditions, the catalytic component such as the acid penetrates to the interior of the fibrous cellulose and promotes hydrolysis. Lowering the amount of catalytic component used also facilitates subsequent purification.

<Particle Shape (Long Diameter/Short Diameter Ratio (L/D Ratio)) of Cellulose>

The cellulose in the cellulose composite of the present invention is preferably in the shape of fine particles. The cellulose particle shape is represented by the ratio (L/D ratio) of the long diameter (L) and short diameter (D) of a particle image obtained by making a pure water suspension having a cellulose composite concentration of 1 mass %, diluting an aqueous dispersion obtained by dispersing by a high-shear homogenizer (manufactured by Nippon Seiki Co., Ltd., product name "Excel Autohomogenizer ED-7," treatment conditions: speed 15,000 rpm×5 minutes) to 0.1-0.5 mass % by pure water, casting on mica, and measuring the dried product by a high-resolution scanning electron microscope (SEM) or atomic force microscope (AFM), and calculated as the average value of 100-150 particles.

L/D is preferably less than 20 in terms of the suspension stability, more preferably 15 or less, even more preferably 10 or less, especially preferably 5 or less, particularly preferably less than 5, and ideally 4 or less. The lower limit of L/D is 1 by definition.

<Anionic Polysaccharide not Having a Chemically Crosslinked Structure>

The polysaccharide in the present invention means a compound in which monosaccharides α or β bond to constitute a main chain or side chain. Monosaccharides include, in addition to sugars such as glucose, galactose, mannose, and xylose, fucose, rhamnose, and other such deoxy sugars, N-acetylglucosamine and other such amino sugars, thio sugars, gluconic acid, galacturonic acid, mannuronic acid, and other such sugar acids, and sugar alcohols. The hydroxyl group of the monosaccharide may be modified by an acetyl group, carboxymethyl group, sulfonic acid group, or other such functional group.

Polysaccharides that themselves become anions due to the release of the cation in water are called anionic polysaccharides. The use of an anionic polysaccharide in the present invention further promotes compositing with cellulose. Examples of natural anionic polysaccharides include gellan gum and xanthan gum containing glucuronic acid, psyllium seed gum containing galacturonic acid, karaya gum containing glucuronic acid and galacturonic acid, and carrageenan containing sulfonated galactose as monosaccharides. Examples of synthetic anionic polysaccharides include carboxymethyl cellulose containing carboxymethylated glucose as the monosaccharide.

Here, "chemically crosslinked structure" in the present invention will be described.

A monomer that bonds with one or two adjacent monomers is defined as a "bonding unit" in a polymer formed by bonding monomers. A monomer that bonds with three or more adjacent monomers is defined as a "branching unit." For example, in a polysaccharide formed by bonding glucose, the glucose that bonds with two adjacent glucoses at position 1 and position 4 corresponds to a bonding unit, and the glucose that bonds with three adjacent glucoses at position 1, position 4, and position 6 corresponds to a branching unit.

The structure of a polymer formed from only bonding units is defined as a linear structure. For example, amylose formed from an end bonding unit formed from glucose that bonds with one adjacent glucose at position 1 or position 4 and a middle bonding unit formed from glucose that bonds with two adjacent glucoses at position 1 and position 4 corresponds to a linear structure.

The structure of a polymer formed from bonding units and branching units in which the branching units are not directly bonded by covalent bonding or ionic bonding is defined as a branched structure. For example, amylopectin having an end bonding unit formed from glucose that bonds with one adjacent glucose at position 1 or position 4, a middle bonding unit formed from glucose that bonds with two adjacent glucoses at position 1 and position 4, and a branching unit formed from glucose that bonds with three adjacent glucoses at position 1, position 4, and position 6 in which the branching units do not form direct covalent bonds or ionic bonds but in which some branching units and bonding units bond, corresponds to a branching structure.

The structure of a polymer formed from bonding units and branching units in which the branching units bond to each other directly by covalent bonding or ionic bonding is defined as a crosslinked structure. For example, carboxymethyl cellulose calcium having an end bonding unit formed from carboxymethylated glucose that bonds with one adjacent carboxymethylated glucose at position 1 or position 4, a middle bonding unit formed from carboxymethylated glucose that bonds with two adjacent carboxymethylated glucoses at position 1 and position 4, and a branching unit formed from a carboxymethylated glucose that bonds with three adjacent carboxymethylated glucoses by glucoside bonds (covalent bonds) at position 1 and position 4 and ionic bonds at position 3 or position 6 in which the branching units ionic bond to each other directly by calcium ions corresponds to a crosslinked structure.
(See each structure below.)

Therefore, the phrase "not having a chemically crosslinked structure" in the present invention means not having a crosslinked structure formed by chemical bonding by covalent bonding or ionic bonding. For example, this means a structure corresponding to the above linear structure or the above branched structure.

[Chemical formula 1]

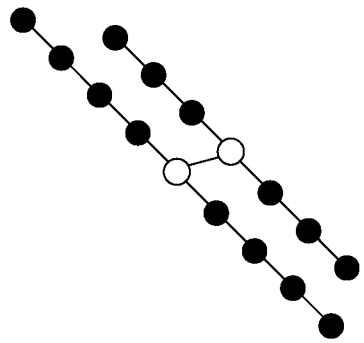

Crosslinked
structure

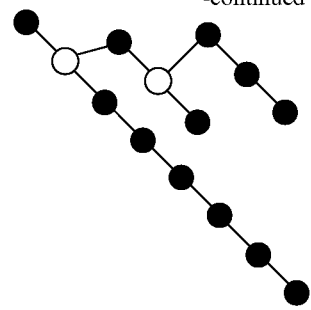

Branched
structure

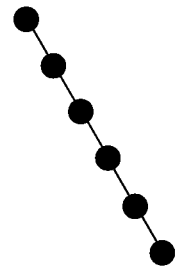

Linear
structure

● Bonding unit
○ Branching unit

The following are suitable as anionic polysaccharides not having a chemically crosslinked structure.

Examples include psyllium seed gum, karaya gum, carrageenan, alginic acid, sodium alginate, HM pectin, LM pectin, *Azotobacter vinelandii* gum, xanthan gum, gellan gum, carboxymethyl cellulose sodium, and other such water-soluble polysaccharides. Carboxymethyl cellulose sodium (also referred to hereinafter as "CMC-Na") and xanthan gum are preferred among these anionic polysaccharides. These anionic polysaccharides may also be used in combinations of two or more types.

<Carboxymethyl Cellulose Sodium>

CMC-Na is preferred among the above anionic polysaccharides for the particular ease of compositing with cellulose. Here, CMC-Na is formed from an anionic polymer, in which some or all of the hydrogen atoms of the hydroxyl groups of cellulose have been substituted by —$CH_2COO$ groups (carboxymethyl groups), and an Na cation, and has a linear chemical structure in which D-glucose is β-1,4-bonded. CMC-Na is obtained, for example, by dissolving pulp (cellulose) by sodium hydroxide solution and etherifying by monochloroacetic acid (or a sodium salt thereof). CMC-Na is a white, fine powder and dissolves rapidly in water. It is utilized as a thickener by taking advantage of its properties.

The use of CMC-Na prepared so that the degree of substitution and viscosity are within the following specific ranges is particularly preferred from the viewpoint of compositing.

The degree of substitution is the degree to which carboxymethyl groups have been ether bonded to the hydroxyl groups (there are three hydroxyl groups per glucose unit) in the CMC-Na, and is preferably 0.6-2.0 per glucose unit. The degree of substitution is preferably within the above range because the higher degree of substitution facilitates compositing with cellulose, increases the storage modulus of the cellulose composite, and can actualize high suspension stability even in aqueous solutions of a high salt concentration (for example, 10 mass % sodium chloride aqueous solution). The degree of substitution is more preferably 0.9-1.3.

The degree of substitution is measured by the following method. Precisely 0.5 g of a sample (anhydride) is weighed out, wrapped in filter paper, and incinerated in a magnetic crucible. After cooling, it is transferred to a 500 mL beaker, and approximately 250 mL of water and 35 mL of 0.05 M sulfuric acid are added and boiled for 30 minutes. After cooling, phenolphthalein indicator is added, the excess acid is back titrated by 0.1 M potassium hydroxide, and the degree of substitution is calculated according to the following formula.

$$\text{Degree of substitution}=(162 \times A)/(10000-80A)$$

$$A=((af-bf1)/\text{sample anhydride (g)})-\text{alkalinity(or+acidity)}$$

Here,

A: Amount of 0.05 M sulfuric acid (mL) consumed by alkali in 1 g of sample
 a: Amount of 0.05 M sulfuric acid used (mL)
 f: Potency of 0.05 M sulfuric acid
 b: Titer of 0.1 M potassium hydroxide (mL)
 f1: Potency of 0.1 M potassium hydroxide
 162: Molecular weight of glucose
 80: Molecular weight of $CH_2COONa-H$.

Alkalinity (or acidity) measurement method: Precisely 1 g of sample (anhydride) is measured out into a 300 mL flask and dissolved by adding approximately 200 mL of water. Five milliliters of 0.05 M sulfuric acid is added, boiled for 10 minutes, then cooled. Phenolphthalein indicator is added, and the solution is titrated by 0.1 M potassium hydroxide (S mL). A blank test (B mL) is conducted simultaneously, and the alkalinity is calculated according to the following formula.

$$\text{Alkalinity}=((B-S) \times f2)/\text{sample anhydride (g)}$$

Here, f2 is the potency of the 0.1 M potassium hydroxide. The value of $(B-S) \times f2$ when negative denotes acidity.

The viscosity of the CMC-Na is preferably 500 mPa·s or less in a 1 mass % pure water solution. Here, the viscosity is measured by the following method. First, CMC-Na powder is dispersed in pure water to make 1 mass % using a high-shear homogenizer (manufactured by Nippon Seiki Co., Ltd., product name "Excel Autohomogenizer ED-7," treatment conditions: speed 15,000 rpm×5 minutes) to prepare an aqueous solution. The aqueous solution obtained is set in a Brookfield viscometer (rotor speed 60 rpm) three hours after dispersion (stored at 25° C.), allowed to stand for 60 seconds, then rotated for 30 seconds and measured. However, the rotor can be changed to suit the viscosity.

The lower the viscosity of the CMC-Na is, the more easily compositing with cellulose is promoted. Therefore, the viscosity of the CMC-Na is more preferably 200 mPa·s or less, and even more preferably 100 mPa·s or less. The lower limit is not particularly set, but the preferred range is 1 mPa·s or higher.

<Water-Absorbent Particles>

Water absorbency is a property whereby a substance retains water. Here, the saturated water absorption, which is the maximum amount of water that can be retained by a substance per unit mass, is used as an index. The saturated water absorption is measured using distilled water in place of oil in accordance with the oil absorption measurement method described in Oil Absorption JIS K5101. The end point is the point at which water starts to separate after the whole has formed one lump.

If the saturated water absorption of the water-absorbent particles is 3 mL per g or higher, it becomes possible to knead the cellulose and anionic polysaccharide by high kneading energy. As a result, the ionic resistance improves, dispersion is stabilized even in beverages blended with a high concentration of ions, and the suspension stability is also excellent. The saturated water absorption of the water-absorbent particles is preferably 4 mL/g or higher, more preferably 6 mL/g or higher. The upper limit is not particularly set, but 25 mL/g or less is preferred.

Furthermore, in measuring the saturated water absorption of the water-absorbent particles, the weight of the water-absorbent particles containing a small amount of water and the water content before measurement of the saturated water absorption are measured, and the weight is converted into the weight in a water-free state. The water content is measured by a weight loss on drying method using an infrared moisture meter. As pretreatment drying, 1.0 g of sample is placed in a weighing bottle and, after spreading uniformly so that the layer thickness is 5 mm or less, dried for three hours by a 105° C. ventilating dryer without capping. The above procedure is repeated to obtain the amount necessary for saturated water absorption measurement.

The size of the water-absorbent particles is preferably 500 μm or less. This is because the water-absorbent particles themselves do not tend to precipitate if the size is 500 μm or less. The lower limit is not particularly restricted, but is preferably 1 μm or more from the viewpoint of compatibility with other components in the cellulose composite when kneading.

The water-absorbent particles in the present invention are preferably particles comprising a compound having a chemically crosslinked structure. "Having a chemically crosslinked structure" in the present invention means having a crosslinked structure formed by chemical bonding by covalent bonding or ionic bonding. The following are suitable as water-absorbent materials having a chemically crosslinked structure.

Examples include carboxymethyl cellulose calcium, calcium alginate, croscarmellose sodium, methacrylate-divinyl benzene potassium copolymer, crosslinked polyvinyl pyrrolidone (PVP), sodium starch glycolate, acetylated adipic acid-crosslinked starch, acetylated phosphoric acid-crosslinked starch, hydroxyalkylated phosphoric acid-crosslinked starch, phosphoric acid-crosslinked starch, phosphoric acid monoesterified phosphoric acid-crosslinked starch, and the like. Carboxymethyl cellulose calcium (CMC-Ca hereinafter), calcium alginate, and the like which can serve as food additives are preferred among these water-absorbent materials.

CMC-Ca having a cellulose skeleton is most preferred among the above water-absorbent particles in terms of compatibility with other components in the cellulose composite.

<Carboxymethyl Cellulose Calcium>

Here, CMC-Ca is formed from an anionic polymer, in which some or all of the hydrogen atoms of the hydroxyl groups of cellulose have been substituted by $-CH_2COO^-$ groups, and a Ca cation, and has a linear chemical structure in which D-glucose is β-1,4-bonded. CMC-Ca can be produced, for example, by dissolving pulp (cellulose) by sodium hydroxide solution, etherifying by monochloroacetic acid (or a sodium salt thereof), then treating with sulfuric acid to produce a free acid insoluble in water, and making a calcium salt by neutralizing by calcium carbonate.

CMC-Ca is a white, fine powder that is insoluble in water and acid and partially dissolves in alkali. The water absorbency is also known to be very high, and it is utilized as a disintegrating agent of tablets by taking advantage of this characteristic. It is also blended with biscuits, cookies, and the like as a molding agent in the food industry field.

The use of CMC-Ca prepared to have a degree of substitution within the following specific range is especially preferred from the viewpoint of compositing. The definition of the degree of substitution is the same as for the CMC-Na above, and the degree of substitution is preferably 0.5-2.0. When the degree of substitution is within the above range, the higher degree of substitution increases the water absorbency and promotes the compositing of the cellulose and anionic polysaccharide. The more preferred degree of substitution is 0.5-0.7.

<Blend Ratio of Water-Absorbent Particles>

The blend ratio of water-absorbent particles in the cellulose composite of the present invention is preferably 0.5-15 mass % based on the relationship between the amount of water absorbed and the kneading energy. The blend ratio is more preferably 0.5-10 mass %, even more preferably 0.5-7 mass %, and especially preferably 0.5-4 mass %. Furthermore, the amount of water-absorbent particles blended is based on the weight of the water-absorbent particles in a water-free state.

<Blend Ratio of Cellulose and Anionic Polysaccharide>

The blend ratio (cellulose/anionic polysaccharide) of cellulose and anionic polysaccharide in the cellulose composite of the present invention is preferably 50-99 parts by mass/1-50 parts by mass. Setting the blend ratio of cellulose and anionic polysaccharide to the above composition promotes compositing, improves the suspension stability in aqueous media having high ionic strength, and achieves an inhibitory effect on the precipitation of water-insoluble components such as functional food materials and the like. The blend ratio of cellulose and anionic polysaccharide in the cellulose composite of the present invention is more preferably 70-99 parts by mass/1-30 parts by mass, even more preferably 80-99 parts by mass/1-20 parts by mass, and especially preferably 85-99 parts by mass/1-15 parts by mass. Furthermore, the amounts of cellulose and anionic polysaccharide blended are each the value based on the weight in a water-free state.

<Viscosity in Sodium Bicarbonate Aqueous Solution>

The viscosity of the cellulose composite when 0.45 g of sodium bicarbonate is dissolved in 100 mL of pure water and a solution containing 1 mass % of the cellulose composite is obtained should be 10 mPa·s or higher so that the cellulose composite has dispersion stability and actualizes a suspension stabilizing effect in beverages blended with a high concentration of ions. The concentration of $NaHCO_3$ (MW=83.98) in this solution is 0.05358 M, and the ionic strength is 0.16. The viscosity can be measured by the following method.

First, 1 mass % (based on the value obtained by measuring the weight and water content and converting to the weight of the cellulose composite in a water-free state) of cellulose composite is dispersed is an aqueous solution in which 0.45 g of sodium bicarbonate (manufactured by Wako Pure Chemical Industries Co., Ltd.) is dissolved in 100 mL of pure water using a high-shear homogenizer (manufactured by Nippon Seiki Co., Ltd., product name "Excel Autohomogenizer ED-7," treatment conditions: speed 15,000 rpm×5 minutes) to prepare a dispersion which is allowed to stand in a 25° C. environment. Next, when the dispersion obtained has stood for one hour, it is set in a Brookfield viscometer (rotor speed 60 rpm), rotated for 30 seconds after standing for 60 seconds, and the viscosity is measured. However, the rotor can be changed to suit the viscosity.

Since the suspension stability of the cellulose composite is better the higher the above viscosity value, the viscosity is preferably 10 mPa·s or higher, more preferably 30 mPa·s or higher, even more preferably 70 mPa·s or higher, especially preferably 100 mPa·s or higher, and most preferably 110 mPa·s or higher. The upper limit of the viscosity is preferably 500 mPa·s or less from the viewpoint of the flavor of the beverage to be suspension stabilized.

<Storage Modulus of Cellulose Composite in Water>

The storage modulus (G') of an aqueous dispersion of the cellulose composite of the present invention is described next. The storage modulus (G') of the cellulose composite of the present invention in an aqueous dispersion of the entire pH 6-7 range containing 1 mass % of cellulose composite is preferably 0.40 Pa or higher. The storage modulus expresses the rheological elasticity of the aqueous dispersion and represents the degree of compositing of the cellulose and anionic polysaccharide or the degree of compositing of the cellulose, anionic polysaccharide, and other water-soluble gum. A higher storage modulus means that compositing of the cellulose and anionic polysaccharide or compositing of the cellulose, anionic polysaccharide, and other water-soluble gum has advanced and means that the network structure of the cellulose composite in the aqueous dispersion is rigid. The more rigid the network structure, the better the suspension stability of the cellulose composite.

The storage modulus in the present invention is the value obtained by dynamic viscoelasticity measurement of an aqueous dispersion (pH 6-7) in which the cellulose composite is dispersed in pure water. In sum, the elastic component that retains the stress stored inside the cellulose composite network structure when strain is applied to the aqueous dispersion is expressed as the storage modulus.

As the method for measuring the storage modulus, the cellulose composite is first dispersed in pure water using a high-shear homogenizer (manufactured by Nippon Seiki Co., Ltd., product name "Excel Autohomogenizer ED-7," treatment conditions: speed 15,000 rpm×5 minutes) to prepare a 1.0 mass % aqueous dispersion. The aqueous dispersion obtained is allowed to stand for three days at room temperature. The strain dependence of the stress of this aqueous dispersion is measured by a viscoelasticity measurement instrument (manufactured by Rheometric Scientific, Inc., model ARES 100FRTN1, geometry: Double Wall Couette, temperature: constant 25.0° C., angular velocity: 20 rad/sec, strain: sweep in the 1→794% range; the aqueous dispersion is supplied slowly using an eyedropper so as not to destroy the microstructures, and measurement is begun in dynamic strain mode after allowing to stand for five minutes). The storage modulus in the present invention is the value of 20% strain on the strain-stress curve obtained by the above measurement. The higher the value of the storage modulus, the more elastic the structures of the aqueous dispersion formed by the cellulose composite, which represents a high level of compositing of the cellulose and anionic polysaccharide or the cellulose, anionic polysaccharide, and other water-soluble gum.

The storage modulus of the cellulose composite is preferably 0.5 Pa or higher, more preferably 1.8 Pa or higher, even more preferably 3.5 Pa or higher, and especially preferably 4.5 Pa or higher.

The upper limit of the storage modulus is not set in particular, but is 6.0 Pa or less considering the ease of drinking when a beverage is made containing the cellulose composite. 6.0 Pa or less is preferred for a light flavor at the amount of cellulose composite added to obtain adequate suspension stability (this varies depending on the beverage, but is, for example, 0.01-1.0 mass % in flavored beverages such as coffee, cocoa, and black tea or in Ca-fortified milk). In addition, when the storage modulus is within this range, water-insoluble components other than cellulose resist aggregation and the like even when the amount of cellulose composite added is lowered (for example, 0.5 mass % or less) to adjust the texture.

<Storage Modulus of Cellulose Composite in Sodium Bicarbonate Aqueous Solution>

The storage modulus (G') of the cellulose composite of the present invention in sodium bicarbonate aqueous solution is described next. The storage modulus (G') of the cellulose composite of the present invention in an aqueous dispersion containing 1 mass % of the cellulose composite in which 0.45 g of sodium bicarbonate is dissolved in 100 mL of pure water is preferably 0.40 Pa or higher.

The method for measuring the storage modulus of the cellulose composite in sodium bicarbonate aqueous solution is the same as the method for measuring the storage modulus described above, except that an aqueous solution obtained by dissolving 0.45 g of sodium bicarbonate in 100 mL of pure water is used instead of pure water.

As was mentioned above, the storage modulus of the cellulose composite in sodium bicarbonate aqueous solution is preferably 0.4 Pa or higher, more preferably 1.0 Pa or higher, even more preferably 1.7 Pa or higher, and especially preferably 2.1 Pa or higher.

<Thixotropy>

The thixotropy of the cellulose composite of the present invention is described next. Thixotropy means a phenomenon whereby a structure is broken down when stirring continues at constant stress and the viscosity of the liquid drops over time, but the structure recovers and returns to its original state over time when the stress is removed. Thixotropy means a behavior (hysteresis) such that the structure when recovered is different from the structure when broken down, and it is said that the greater the hysteresis area is, the larger the thixotropy is, and the material presents good characteristics such as good texture and the like.

As the method for measuring the thixotropy, the cellulose composite is first dispersed in pure water using a high-shear homogenizer (manufactured by Nippon Seiki Co., Ltd., product name "Excel Autohomogenizer ED-7," treatment conditions: speed 15,000 rpm×5 minutes) to prepare a 0.5 mass % aqueous dispersion. The aqueous dispersion obtained is allowed to stand for three days at room temperature. The stress of this aqueous dispersion when the shear rate is raised and lowered is measured by a viscoelasticity measurement instrument (manufactured by Rheometric Scientific, Inc., model ARES 100FRTN1, geometry: Double Wall Couette, temperature: constant 25.0° C., final shear rate: 200 s$^{-1}$, zone time: 60 s, pre-test holding time: 600 s; the aqueous dispersion is supplied slowly using an eyedropper so as not to destroy the microstructures). The shear stress (stress [Pa]) when the shear rate is 200→0 [1/s] (the shear rate is lowered one by one from 200, finally to 0 (1/s)) from the shear stress (stress [Pa]) when the shear rate is 0→200 [1/s] (the shear rate is raised one by one, finally to 200 (1/s)) is determined for the hysteresis area. The loop area (Pa/s) is determined by the trapezoidal rule.

The hysteresis area of the cellulose composite is preferably 1500 or higher, more preferably 3300 or higher, and even more preferably 4500 or higher. The upper limit is not particularly set, but a realistic range is 10,000 or lower.

<Colloidal Cellulose Composite Content of Cellulose Composite>

The cellulose composite of the present invention preferably contains 50 mass % or more colloidal cellulose composite. Here, colloidal cellulose composite means the solids fraction (including cellulose and anionic polysaccharide) present in the supernatant after centrifugation when the cellulose composite is made into a 0.5 mass % pure water suspension, dispersed by a high-shear homogenizer (manufactured by Nippon Seiki Co., Ltd., product name "Excel Autohomogenizer ED-7," treatment conditions: speed 15,000 rpm×5 minutes), and centrifuged (manufactured by Kubota Shoji Co., Ltd., product name "model 6800 Centrifuge" Rotor-type RA-400, treatment conditions: centrifuged for 10 minutes at a centrifugal force of 39,200 m$^2$/s, the supernatant collected, and the supernatant then centrifuged for 45 minutes at 116,000 m$^2$/s). The colloidal cellulose composite content is the mass percentage of colloidal cellulose composite to the total cellulose composite. Since colloidal cellulose composite is less likely to precipitate during storage than the coarse particles precipitated by centrifugation, the suspension stability improves when the colloidal cellulose composite content is 50 mass % or higher. The colloidal cellulose composite content is preferably 60 mass % or higher, more preferably 70 mass % or higher, and especially preferably 80 mass % or higher. Since the higher the colloidal cellulose composite content, the higher the suspension stability is, the upper limit is not particularly restricted, but a preferred limit is 100 mass % or less.

<Spread of Cellulose Composite Anionic Polysaccharide—Median Diameter by Dynamic Light Scattering—>

The cellulose composite of the present invention is characterized in that the spread of the anionic polysaccharide extending radially from the cellulose particle surface is large when made into an aqueous dispersion. This spread of the anionic polysaccharide is represented by the median diameter measured by dynamic light scattering in the colloidal cellulose composite. The median diameter in the cellulose composite of the present invention is preferably 0.85 μm or higher.

This median diameter by dynamic light scattering can be measured by the following method. First, the cellulose composite is made into a 0.5 mass % pure water suspension, dispersed by a high-shear homogenizer (manufactured by Nippon Seiki Co., Ltd., product name "Excel Autohomogenizer ED-7," treatment conditions: speed 15,000 rpm×5 minutes), centrifuged (manufactured by Kubota Shoji Co., Ltd., product name "model 6800 Centrifuge" Rotor-type RA-400, treatment conditions: centrifuged for 10 minutes at a centrifugal force of 39,200 m$^2$/s, the supernatant collected, and the supernatant then centrifuged for 45 minutes at 116,000 m$^2$/s), and the supernatant collected after centrifugation. Furthermore, this centrifugation removes coarse particles that do not contribute to improving the suspension stability and are precipitated by centrifugation and recovers the colloidal cellulose particles that contribute to improving the suspension stability. Next, the collected supernatant is placed in a 50 mL PP sample tube and sonicated for 10 minutes by an ultrasonic cleaner (manufactured by As One Corporation, product name model AUC-1L). The particle size distribution (frequency distribution of scattering intensity to particle diameter value) is measured by a zeta potential-particle diameter measurement system (manufactured by Otsuka Electronics Co., Ltd., product name "ELSZ-2" (batch cell)). Here, the median diameter is the particle diameter value (μm) corresponding to 50% scattering intensity integration in this frequency distribution. Since the larger the median diameter of the colloidal cellulose composite, the better the suspension stability of the cellulose composite is, the median diameter is preferably 1.5 μm or higher, more preferably 2.0 μm or higher, and even more preferably 2.5 μm or higher. The upper limit is not particularly restricted, but is preferably 5.0 μm or lower.

<Method for Producing Cellulose Composite>

The method for producing the cellulose composite of the present invention is described next. The cellulose composite of the present invention is obtained by mixing cellulose, anionic polysaccharide, and water-absorbent particles thoroughly and compositing these components. However, the cellulose composite of the present invention is preferably obtained by applying mechanical shear force to the cellulose and anionic polysaccharide in the presence of water-absorbent particles in the kneading step, and making the cellulose fine together with compositing the anionic polysaccharide on the cellulose surface. Compositing by thoroughly kneading the anionic polysaccharide into fine cellulose in particular is necessary to obtain a cellulose composite having a median diameter of the above-specified value or above.

Water-soluble gums and hydrophilic substances other than the anionic polysaccharide and other additives may also be added during kneading. The material that has been subjected to the above treatment is dried as needed. The cellulose composite of the present invention may have any form, such as undried or subsequently dried after being subjected to the above mechanical shear.

A method of kneading using a kneading machine or the like can be used to apply mechanical shear force. A kneader, extruder, planetary mixer, crusher, or the like can be used as a kneading machine, and may be either a continuous or a batch type. The temperature during kneading need not necessarily be set within a specific range, but kneading may be carried out while removing heat when heat is generated by the compositing reaction, friction, or the like during kneading. These devices may be used individually, or two or more types of device may be used in combination. These devices may be selected as is appropriate depending on the viscosity requirement and the like in various applications.

However, a lower kneading temperature is preferred for suppressing deterioration of the anionic polysaccharide and raising the storage modulus (G') of the cellulose composite obtained as a result. The kneading temperature is preferably 0-100° C., more preferably 90° C. or lower, especially preferably 70° C. or lower, even more preferably 60° C. or lower, and most preferably 50° C. or lower. One may also freely devise heat removal by jacket cooling, heat radiation, and the like to maintain the above kneading temperature under high energy.

As was mentioned above, the addition of water-absorbent particles absorbs the water contained in the kneaded material and can effectively raise the solids fraction during kneading. The solids fraction during kneading (percentage of the dry mass of the kneaded material to the mass of the kneaded material) is preferably set at 20 mass % or higher. Kneading the kneaded material in a high-viscosity, semi-solid state is preferred because it prevents the kneaded material from becoming loose, facilitates transmission of the kneading energy described below to the kneaded material, and promotes compositing. The solids fraction during kneading is more preferably 30 mass % or higher, even more preferably 40 mass % or higher, and especially preferably 50 mass % or higher. The upper limit is not particularly restricted, but a realistic range is preferably 90 mass % or lower in consideration of obtaining an adequate kneading effect and uniformly kneaded state without the kneaded material forming a discontinuous granular state with a low water content. The realistic range is more preferably 70 mass % or lower, even more preferably 60 mass % or lower. As regards the timing of water addition to bring the solids fraction within the above range, the necessary amount of water may be added before the kneading step, water may be added during the kneading step, or both may be done.

Here, the solids fraction is the solids fraction obtained by a weight loss on drying method. A kneaded material of a predetermined mass in a moist state is dried, and the solids fraction is calculated by the following formula based on the mass of the water evaporated. Solids fraction=(100−(amount of water evaporated (g)/mass of kneaded material in a moist state (g)×100)) (mass %). For example, the solids fraction calculated using the above formula from the water content obtained by finely crushing 2.0 g of kneaded material to a diameter of 5 mm or less and using an infrared moisture meter (Kett Electric Laboratory, model FD-240, heated for 30 minutes at 105° C.) can be used.

The kneading energy will be described here. The kneading energy is defined as the electrical energy (Wh/kg) consumed by the kneading machine per unit mass of kneaded material. The kneading energy is preferably 50 Wh/kg or higher. As long as the kneading energy is 50 Wh/kg or higher, the grinding property exerted on the kneaded material is high, compositing of the cellulose and anionic polysaccharide or the cellulose, anionic polysaccharide, and other water-soluble gum and the like advances, and the suspension stability of the neutral cellulose composite improves. The kneading energy is more preferably 80 Wh/kg or higher, even more preferably 100 Wh/kg or higher, especially preferably 200 Wh/kg or higher, still more preferably 300 Wh/kg or higher, and most preferably 400 Wh/kg or higher.

The higher kneading energy is thought to promote the compositing of the cellulose and anionic polysaccharide. However, the upper limit of the kneading energy is preferably 1000 Wh/kg since the equipment becomes industrially excessive and the burden on the equipment becomes excessive when the kneading energy is too high.

The degree of compositing is thought to be the proportion of hydrogen bonding between the cellulose and the anionic polysaccharide and other components. As compositing progresses, the proportion of hydrogen bonding increases, and the effects of the present invention improve. In addition, progress in compositing increases the median diameter of the colloidal cellulose composites contained in the cellulose composite.

Examples of the method of introducing the raw material during kneading include a method of introducing the cellulose and anionic polysaccharide and water-absorbent particles simultaneously and compositing, and a method of first kneading the cellulose and water-absorbent particles, introducing the anionic polysaccharide after the solids fraction of the cellulose has increased substantially, and compositing. The most preferred method, however, is to introduce the water-absorbent particles after compositing the cellulose and anionic polysaccharide, to substantially increase the overall solids fraction and further promote compositing. Each method as above may be performed in multiple stages.

A known drying method such as shelf drying, spray drying, belt drying, fluidized bed drying, freeze drying, microwave drying, and the like can be used when drying the kneaded material obtained from the kneading step described above to obtain the cellulose composite of the present invention. It is preferable when supplying the kneaded material to the drying step to maintain the solids fraction concentration of the kneading step and supply the kneaded material to the drying step without adding water.

The water content of the cellulose composite after drying is preferably 1-20 mass %. Making the water content 20 mass % or less reduces the likelihood of problems such as stickiness and decay and problems of cost in transport. The water content is more preferably 15 mass % or less, and especially preferably 10 mass % or less. In addition, there is no deterioration of dispersibility due to excessive drying when the water content is 1 mass % or higher. The water content is more preferably 1.5 mass % or higher.

Since a powder is an easy shape to handle when the cellulose composite is distributed on the market, the cellulose composite obtained by drying is preferably made into a powder by pulverization. However, when spray drying is used as the drying method, pulverization need not be performed since drying and powdering occur simultaneously. A known method such as a cutter mill, hammer mill, pin mill, jet mill, or the like can be used when pulverizing the dried cellulose composite. The degree of pulverization is such that the pulverized powder all passes through a 1 mm mesh sieve. More preferably, all of the powder passes through a 425 μm mesh sieve, and the powder is preferably pulverized so that the average particle size (weight average particle diameter) is 10-250 μm. The fine particles of cellulose composite in these dry powders aggregate and form secondary aggregates. These secondary aggregates break down when stirred in water, and disperse in the above cellulose composite fine particles. The apparent weight average particle diameter of the secondary aggregates is the cumulative weight 50% particle diameter in the particle size distribution obtained by sieving 10 g of sample for 10 minutes using a Ro-tap sieve shaker (manufactured by Taira Kosakusho, Ltd., model A sieve shaker) and a JIS standard sieve (Z8801-1987).

The dried cellulose composite disperses easily when stirred in water, and a stable colloidal dispersion having a smooth texture and no grittiness in which the cellulose is dispersed uniformly is formed. Since a stable colloidal dispersion forms with no aggregation or separation of the cellulose at neutral in particular, it functions well as a stabilizer and the like.

<Use>

The cellulose composite of the present invention can be used in various food products. Examples include coffee, black tea, matcha, cocoa, sweet red bean soup, juice, and other such flavored beverages; raw milk, processed milk, lactic acid bacteria beverages, soy milk, and other such milky beverages; calcium-fortified beverages and other such nutrient-fortified beverages; and various beverages including dietary fiber-containing beverages; ice cream, ice milk, soft cream, milk shake, sherbet, and other such frozen confections; butter, cheese, yoghurt, coffee whitener, whipped cream, custard cream, pudding, and other such dairy products; mayonnaise, margarine, spreads, shortening, and other such fats/oils processed foods; various soups, stews, sauces, dipping sauces, dressings, and other such seasonings; various paste spices typified by mustard paste; various fillings typified by jams and flour paste; various bean jams; gel and paste-like foods including jellies; cereal food products including breads, noodles, pastas, pizzas, and various premixes; Western and Japanese sweets including candies, cookies, biscuits, hot cakes, chocolate, and rice cakes; various marine product pastes typified by kamaboko, hanpen, and the like; livestock products typified by ham, sausage, ground beef, and the like; cream croquettes, Chinese bean jam, gratins, dumplings, and various other prepared foods; delicacies such as salted fish, pickled vegetables, and the like; pet foods; and parenteral liquid diets, and the like.

The cellulose composite of the present invention can be used as a suspension stabilizer, emulsion stabilizer, thickening stabilizer, foam stabilizer, clouding agent, texture-imparting agent, fluidity-improving agent, shape-retaining agent, water separation inhibitor, texture-modifying agent, powdered base, dietary fiber base, or a fat substitute or other such low-calorie base in these uses. In addition, the effects of the present invention are actualized even when the form of the above foods or the method of preparation is different, such as retort foods, powdered foods, frozen foods, microwaveable foods, and the like. In particular, the fact that the cellulose composite functions even in a heated environment, low pH environment, and high salt-concentration environment differs from conventional cellulosic materials.

When the cellulose composite of the present invention is used in foods, each food may be prepared using commonly used methods and the same equipment to combine the cellulose composite with the main raw material and, as needed, flavorings, pH regulators, thickening stabilizers, salts, sugars, fats and oils, proteins, emulsifiers, acidulants, colorings, and the like and to conduct procedures such as mixing, kneading, stirring, emulsifying, heating, and the like.

In particular, the cellulose composite of the present invention is especially suitable as a suspension stabilizer of liquid foods and beverages containing a large amount of minerals since it disperses stably even in media blended with a high concentration of minerals, that is, ions, has a high storage modulus (G'), and has excellent suspension stability. Specifically, the cellulose composite is preferred as a suspension stabilizer of liquid foods and beverages having an ionic strength of 0.1 or higher, and more preferred as a suspension stabilizer of liquid foods and beverages having an ionic strength of 0.2 or higher. There is no upper limit to the ionic strength of the ionic beverage or liquid food used as long as the cellulose composite of the present invention manifests an effect, but 1.0 can be given as an example. Furthermore, examples of beverages having an ionic strength of 0.2 or higher include beverages with sodium bicarbonate added and beverages having a high mineral concentration such as cocoa, black tea, coffee extract, and the like.

<Method for Adding Cellulose Composite>

Examples of the method of adding the cellulose composite of the present invention to foods and beverages include dispersing the cellulose composite of the present invention in water at the same time as the main raw materials or coloring materials, flavorings, acidulants, thickening agents, and other such components.

In addition, when a dry powder of the cellulose composite is dispersed in an aqueous medium, it is preferable for improving the suspension stability of the cellulose composite to first disperse the cellulose composite in water, then add it to the target food form. When the cellulose composite is a dry powder, the method for dispersing it in water can be to disperse it using various dispersing machines, emulsifying machines, grinding machines, or other such kneading machines commonly used in the production process of foods and the like. Dispersing machines and emulsifying machines typified by a propeller stirring machine, high-speed mixer, homomixer, cutter, and other such various mixers; ball mill, colloid mill, bead mill, crusher, or other such mills; high-pressure homogenizer, nanomizer, and other such high-pressure homogenizers; and kneading machines typified by a planetary mixer, kneader, extruder, turbulizer, and the like can be used as concrete examples of the kneading machine. Two or more kneading machines may be used in combination. Conducting the procedure while heating also facilitates dispersion.

<Amount Added to Foods and Beverages>

The cellulose composite of the present invention can be used added, for example, to coffee, cocoa, milk, and other such beverages, and can preferably be used even in coffee beverages in which it was difficult for cellulose composites of the prior art to manifest an effect. The amount of cellulose composite added to foods and beverages is not particularly restricted, but is preferably 0.01 mass % or higher. Setting the amount of cellulose composite added at 0.01 mass % or higher increases the dispersion and suspension stability, and has an excellent effect on emulsification stability and preventing water separation. The amount of cellulose composite added is more preferably 0.05 mass % or higher, even more preferably 0.1 mass % or higher. The amount of cellulose composite added is preferably 5 mass % or lower so as not to trigger aggregation or separation and in terms of the drinking ease (throat passage, grittiness on tongue) of the beverage.

<Insoluble Components>

The cellulose composite of the present invention is especially suitable for neutral foods and beverages containing water-insoluble components. Water-insoluble components are components that do not dissolve in water and means those that pass through a 10 mm mesh sieve in the present invention. Components that pass through a 5 mm mesh sieve are more suitable, and those that pass through a 2 mm mesh sieve are even more suitable. Water-insoluble components become unstable at neutral, but addition of the cellulose composite of the present invention obtains excellent suspension stability.

Examples of water-insoluble components include proteins in food and beverages, or fruit scraps, lactic acid bacteria contained in lactic acid bacteria beverages and the like, pulp in fruit and vegetable beverages, milk calcium, calcium carbonate, beta-glucan, proteins (soybean protein, milk protein, collagen), turmeric, reishi, and other such functional food materials having a specific gravity higher than water, coenzyme Q10 and other such ubidecarenone compounds, docosahexaenoic acid, eicosapentaenoic acid, esters thereof, and other such omega 3 compounds, ceramide compounds, and other such functional food materials having a specific gravity lower than water, and the like.

The above functional food materials are preferably added in an amount of 0.01 mass % or higher relative to the beverage, although it also depends on the daily intake of the beverage and the effectiveness of the material. The amount added is more preferably 0.05 mass % or higher, and even more preferably 0.1 mass % or higher.

<Natural Concentrated Liquid Foods>

The cellulose composite of the present invention is also suitable for liquid foods. Here, liquid foods are those generally called natural concentrated liquid foods, are prepared by adding minerals, dietary fiber, and vitamins to a natural food base to make 1 kcal or more per milliliter, and are liquid foods intended mainly for infants or adults with severe diseases. Since such natural concentrated liquid foods are made using a high-concentration natural food as the base, they generate a residue easily. The residue precipitates and tends to cause problems such as making it difficult for the liquid food to pass through a tube or the minerals and proteins included in components react during heat sterilization of the liquid food, generating aggregates. Addition of the cellulose composite of the present invention to such natural concentrated liquid foods can solve these problems, obtain a stable natural concentrated liquid food, and suppress generation of aggregates during heat sterilization.

<Beverages to Prevent Heat Stroke>

The cellulose composite of the present invention is also suitable for beverages to prevent heat stroke in which a higher concentration of minerals is blended than in ordinary beverages. According to the Ministry of Health, Labor, and Welfare, one should drink 1-2 cups of an oral rehydration solution containing 40-80 mg of sodium per 100 mL every 20-30 minutes during the summer when cases of heat stroke increase. In coffee, black tea, matcha, cocoa, sweet bean soup, juices, and other such flavored beverages, raw milk, processed milk, lactic acid bacteria beverages, soy milk, and other such milky beverages that satisfy the above sodium content conditions, the sodium present in ionic form and proteins and the like in the components react and generate aggregates. In addition, even when a stabilizer is combined to prevent the generation of aggregates, the stabilizer generally becomes unstable as the mineral fraction becomes high, and the stabilizer itself precipitates. This results in the problem of precipitation of proteins and other such water-insoluble components. Adding the cellulose composite of the present invention to such beverages, however, solves these problems and makes it possible to obtain a stable beverage to prevent heat stroke.

<Uses Other than Foods>

The cellulose composite of the present invention has markedly improve colloid dispersibility, and examples of uses other than foods include syrups, liquids, ointments, and other such pharmaceutical products; lotions, emulsions, cleansers, and other such cosmetics; cleansers and treatment agent raw materials for food products and industry, household detergent raw materials (for clothes, kitchen, house, tableware, and the like), paints, pigments, ceramics, water-based latex, for emulsification (polymerization), for agricultural chemicals, for fiber processing (refining agents, dye auxiliaries, softeners, water repellents), soil-release finishing agents, admixtures for concrete, for printing ink, for lubricating oils, antistatic agents, anti-fogging agents, lubricants, dispersants, deinking agents, and other such industrial products. Compositions among them in particular in which a high concentration of structural components are present in an ionic state can maintain a stable dispersed state without aggregation or separation, water separation, or generating a precipitate. The cellulose composite can also be used in a wide range of food products other than those mentioned above since the problem of grittiness has been solved by its smooth feeling and body feeling, together with its remarkably improved performance as a stabilizer.

The present invention is described below through examples. However, these examples in no way limit the scope of the present invention.

EXAMPLES

<Method for Measuring Average Degree of Polymerization of Cellulose>

The average degree of polymerization of the cellulose was measured by a reduced specific viscosity method by copper ethylenediamine solution as stipulated in the "14$^{th}$ Revised Japan Pharmacopoeia," (published by Hirokawa Shoten) microcrystalline cellulose identification test (3).

<Viscosity of Carboxymethyl Cellulose Sodium (CMC-Na)>

(1) CMC-Na powder was dispersed in pure water to make 1 mass % using a high-shear homogenizer (manufactured by Nippon Seiki Co., Ltd., product name "Excel Autohomogenizer ED-7," treatment conditions: speed 15,000 rpm×5 minutes), and an aqueous solution was prepared.

(2) The aqueous solution obtained was set in a Brookfield viscometer (rotor speed 60 rpm) three hours after dispersion (stored at 25° C.), allowed to stand for 60 seconds, then rotated for 30 seconds and measured. However, the most suitable rotor can be used in accordance with the viscosity.

<Degree of Substitution of Carboxymethyl Cellulose Sodium (CMC-Na)>

(1) Precisely 0.5 g of sample (anhydride) was weighed out, wrapped in filter paper, and incinerated in a magnetic crucible.

(2) After cooling, it was transferred to a 500 mL beaker, and approximately 250 mL of water and 35 mL of 0.05 M sulfuric acid were added and boiled for 30 minutes. After cooling, phenolphthalein indicator was added, the excess acid was back titrated by 0.1 M potassium hydroxide, and the degree of substitution was calculated according to the following formula.

$$\text{Degree of substitution} = (162 \times A)/(10000 - 80A)$$

$$A = ((af - bf1)/\text{sample anhydride (g)}) - \text{alkalinity(or+ acidity)}$$

Here,

A: Amount of 0.05 M sulfuric acid (mL) consumed by alkali in 1 g of sample a: Amount of 0.05 M sulfuric acid used (mL)

f: Potency of 0.05 M sulfuric acid b: Titer of 0.1 M potassium hydroxide (mL)

f1: Potency of 0.1 M potassium hydroxide

162: Molecular weight of glucose

80: Molecular weight of $CH_2COONa$—H

Alkalinity (or acidity) measurement method: Precisely 1 g of sample (anhydride) was measured out into a 300 mL flask and dissolved by adding approximately 200 mL of water. Five milliliters of 0.05 M sulfuric acid was added, boiled for 10 minutes, then cooled. Phenolphthalein indicator was added, and the solution was titrated by 0.1 M potassium hydroxide (S mL). A blank test (B mL) was conducted simultaneously, and the alkalinity was calculated according to the following formula.

$$\text{Alkalinity} = ((B - S) \times f)/\text{sample anhydride (g)}$$

Here, f is the potency of the 0.1 M potassium hydroxide. The value of (B−S)×f when negative denotes acidity.

<Saturated Water Absorption of Water-Absorbent Particles>

The saturated water absorption was measured using distilled water in place of oil in accordance with the oil absorption measurement method described in Oil Absorption JIS K5101. The end point was the point at which water started to separate after the whole had formed one lump <Particle Shape (L/D) of Cellulose>

An aqueous dispersion obtained by making the cellulose composite into a 1 mass % pure water suspension and dispersing by a high-shear homogenizer (manufactured by Nippon Seiki Co., Ltd., product name "Excel Autohomogenizer ED-7," treatment conditions: speed 15,000 rpm×5 minutes) was diluted to 0.1 mass % by pure water, and one drop was cast on mica using an eyedropper. The excess water was driven off by an air duster, followed by air drying to prepare a sample. The long diameter (L) and short diameter (D) were determined from the shape of particles having a long diameter (L) of 2 μm or less based on images measured by an atomic force microscope (instrument manufactured by Digital Instruments, Inc., Nano Scope IV MM, scanner EV, measurement mode: Tapping, probe: NCH silicon single crystal probe). The ratio (L/D) is the shape of the cellulose particle and was calculated as the average value of 100-150 particles.

<Storage Modulus of Cellulose Composite>

(1) The cellulose composite was dispersed in pure water using a high-shear homogenizer (manufactured by Nippon Seiki Co., Ltd., product name "Excel Autohomogenizer ED-7," treatment conditions: speed 15,000 rpm×5 minutes), and a 1.0 mass % pure water dispersion was prepared. The aqueous dispersion obtained was allowed to stand for three days at room temperature.

(2) The strain dependence of the stress of this aqueous dispersion was measured by a viscoelasticity measurement instrument (manufactured by Rheometric Scientific, Inc., model ARES 100FRTN1, geometry: Double Wall Couette, strain: sweep in the 1→794% range). The storage modulus (G') in the present invention is the value of 20% strain on the strain-stress curve obtained by the above measurement.

<Storage Modulus of Cellulose Composite in Sodium Bicarbonate Aqueous Solution>

(1) The cellulose composite was dispersed to make 1 mass % (based on the value obtained by measuring the weight and the water content and converting to the weight of the cellulose composite in a water-free state) in an aqueous solution obtained in advance by dissolving 0.45 g of sodium bicarbonate (manufactured by Wako Pure Chemical Industries Co., Ltd.) in 100 mL of pure water, using a high-shear homogenizer (manufactured by Nippon Seiki Co., Ltd., product name "Excel Autohomogenizer ED-7," treatment conditions: speed 15,000 rpm×5 minutes), and a 1.0 mass % dispersion was prepared. The aqueous dispersion obtained was allowed to stand for three days at room temperature.

(2) The strain dependence of the stress of this aqueous dispersion was measured by a viscoelasticity measurement instrument (manufactured by Rheometric Scientific, Inc., model ARES 100FRTN1, geometry: Double Wall Couette, temperature: constant 25.0° C., angular velocity: 20 rad/sec, strain: sweep in the 1→794% range). The storage modulus (G') in the present invention is the value of 20% strain on the strain-stress curve obtained by the above measurement.

<Colloidal Cellulose Composite Content of Cellulose Composite>

(1) The cellulose composite was made into a 0.5 mass % pure water suspension and dispersed using a high-shear homogenizer (manufactured by Nippon Seiki Co., Ltd., product name "Excel Autohomogenizer ED-7," treatment conditions: speed 15,000 rpm×5 minutes).

(2) This dispersion was centrifuged (manufactured by Kubota Shoji Co., Ltd., product name "model 6800 Centrifuge" Rotor-type RA-400, treatment conditions: centrifuged for 10 minutes at a centrifugal force of 39,200 $m^2/s$, the supernatant collected, and the supernatant then centrifuged for 45 minutes at 116,000 $m^2/s$).

(3) The centrifuged supernatant was placed in a glass weighing bottle and dried for 15 hours at 60° C., then for two hours at 105° C. The weight was measured after reaching constant weight in a desiccator. In addition, an uncentrifuged aqueous dispersion was separately dried in the same way, and the weight was measured. The mass percentage of cellulose solids fraction remaining in the supernatant was determined by the following formula from these results. Formula for calculating colloidal cellulose composite content: (solids fraction of 50 g of supernatant obtained by centrifuging 50 g of uncentrifuged product)/(solids fraction of 50 g of uncentrifuged product)×100

<Median Diameter of Colloidal Cellulose Composite by Dynamic Light Scattering>

(1) The cellulose composite was made into a 0.5 mass % pure water suspension, dispersed by a high-shear homogenizer (manufactured by Nippon Seiki Co., Ltd., product name "Excel Autohomogenizer ED-7," treatment conditions: speed 15,000 rpm×5 minutes), centrifuged (manufactured by Kubota Shoji Co., Ltd., product name "model 6800 Centrifuge" Rotor-type RA-400, treatment conditions: centrifuged for 10 minutes at a centrifugal force of 39,200 $m^2/s$, the supernatant collected, and the supernatant then centrifuged for 45 minutes at 116,000 $m^2/s$), and the centrifuged supernatant was collected.

(2) The supernatant was placed in a 50 mL PP sample tube and sonicated for 10 minutes by an ultrasonic cleaner (manufactured by As One Corporation, product name model AUC-1L).

(3) The particle size distribution (frequency distribution of scattering intensity to particle diameter value) was measured by a zeta potential-particle diameter measurement system (manufactured by Otsuka Electronics Co., Ltd., product name "ELSZ-2" (batch cell)). Here, the median diameter is the particle diameter value (μm) corresponding to 50% scattering intensity integration in this frequency distribution.

<Thixotropy>

(1) As the method for measuring the thixotropy, the cellulose composite was first dispersed in pure water using a high-shear homogenizer (manufactured by Nippon Seiki Co., Ltd., product name "Excel Autohomogenizer ED-7," treatment conditions: speed 15,000 rpm×5 minutes) to prepare a 0.5 mass % pure aqueous dispersion. The aqueous dispersion obtained was allowed to stand for three days at room temperature.

(2) The stress of this aqueous dispersion when the shear rate was raised and lowered was measured by a viscoelasticity measurement instrument (manufactured by Rheometric Scientific, Inc., model ARES 100FRTN1, geometry: Double Wall Couette, temperature: constant 25.0° C., final shear rate: 200 $s^{-1}$, zone time: 60 s, pre-test holding time: 600 s). The shear stress (stress [Pa]) when the shear rate is 200→0 [1/s] (the shear rate is lowered one by one from 200, finally to 0 (1/s)) from the shear stress (stress [Pa]) when the shear rate is 0→200 [1/s] (the shear rate is raised one by one, finally to 200 (1/s)) was determined for the hysteresis area. The loop area (Pa/s) was determined by the trapezoidal rule.

<Viscosity in Sodium Bicarbonate Aqueous Solution>

(1) The cellulose composite was dispersed to make 1 mass % (based on the value obtained by measuring the weight and water content and converting to the weight of the cellulose composite in a water-free state) in an aqueous solution in which 0.45 g of sodium bicarbonate (manufactured by Wako Pure Chemical Industries Co., Ltd.) was dissolved in 100 mL of pure water in advance, using a high-shear homogenizer (manufactured by Nippon Seiki Co., Ltd., product name "Excel Autohomogenizer ED-7," treatment conditions: speed 15,000 rpm×5 minutes), and a 1.0 mass % dispersion was prepared.

(2) The aqueous dispersion obtained was set in a Brookfield viscometer (rotor speed 60 rpm) one hour after dispersion (stored at 25° C.), allowed to stand for 60 seconds, rotated for 30 seconds, and measured. However, the most suitable rotor can be used depending on the viscosity.

Example 1

Commercial dissolving pulp (DP pulp) was chopped, then hydrolyzed for 15 minutes at 105° C. in 2.5 mol/L hydrochloric acid, then washed with water and filtered to produce wet cake cellulose having a solids fraction of 50 mass % (the average degree of polymerization was 220).

Next, the wet cake cellulose, commercial CMC-Na (viscosity of a 1% solution: 55 mPa·s, degree of etherification: 1.0-1.3), and commercial CMC-Ca (amount of water absorbed 6 g per gram) were prepared and introduced into a planetary mixer (manufactured by Shinagawa Kogyosho, 5DM-03-R, hook type stirring blades) to make a cellulose (MCC hereinafter)/CMC-Na/CMC-Ca mass ratio (based on the values obtained by measuring the weight and water content and converting to the weight of the component in a water-free state) of 84/15.5/0.5, and water was added to make a solids fraction of 45 mass %.

The contents were subsequently kneaded at 126 rpm, and a cellulose composite A was obtained. The kneading energy was controlled by the kneading time of the planetary mixer, and the actual measured value was 40 Wh/kg. The temperature of the kneaded material was measured directly using a thermocouple, and the kneading temperature was 20-40° C. throughout kneading.

The particle L/D of the cellulose composite A obtained was 1.6. The storage modulus (G') was 0.7 Pa, the storage modulus in sodium bicarbonate aqueous solution was 0.4 Pa, the colloidal cellulose composite content was 68 mass %, the dynamic light scattering median diameter of the colloidal cellulose composites was 1.5 μm, the thixotropy was 640, and the viscosity in sodium bicarbonate aqueous solution was 10 mPa·s. The results are shown in Table 1.

Example 2

Commercial DP pulp was chopped, then hydrolyzed for 15 minutes at 105° C. in 2.5 mol/L hydrochloric acid, then washed with water and filtered to produce wet cake cellulose having a solids fraction of 50 mass % (the average degree of polymerization was 220).

Next, the wet cake cellulose, commercial CMC-Na (viscosity of a 1% solution: 55 mPa·s, degree of etherification: 1.0-1.3), and commercial CMC-Ca (amount of water absorbed 6 g per gram) were prepared and introduced into a planetary mixer (manufactured by Shinagawa Kogyosho, 5DM-03-R, hook type stirring blades) to make an MCC/CMC-Na/CMC-Ca mass ratio of 84/14/2.0, and water was added to make a solids fraction of 45 mass %.

The contents were subsequently kneaded at 126 rpm, and a cellulose composite B was obtained. The kneading energy was controlled by the kneading time of the planetary mixer, and the actual measured value was 50 Wh/kg. The temperature of the kneaded material was measured directly using a thermocouple, and the kneading temperature was 20-40° C. throughout kneading.

The particle L/D of the cellulose composite B obtained was 1.6. The storage modulus (G') was 1.7 Pa, the storage modulus in sodium bicarbonate aqueous solution was 1.0 Pa, the colloidal cellulose composite content was 73 mass %, the dynamic light scattering median diameter of the colloidal cellulose composites was 1.7 μm, the thixotropy was 1560, and the viscosity in sodium bicarbonate aqueous solution was 30 mPa·s. The results are shown in Table 1.

Example 3

Commercial DP pulp was chopped, then hydrolyzed for 15 minutes at 105° C. in 2.5 mol/L hydrochloric acid, then washed with water and filtered to produce wet cake cellulose having a solids fraction of 50 mass % (the average degree of polymerization was 220).

Next, the wet cake cellulose, commercial CMC-Na (viscosity of a 1% solution: 55 mPa·s, degree of etherification: 1.0-1.3), and commercial CMC-Ca (amount of water absorbed 6 g per gram) were prepared and introduced into a planetary mixer (manufactured by Shinagawa Kogyosho, 5DM-03-R, hook type stirring blades) to make an MCC/CMC-Na/CMC-Ca mass ratio of 84/13.5/2.5, and water was added to make a solids fraction of 45 mass %.

The contents were subsequently kneaded at 126 rpm, and a cellulose composite C was obtained. The kneading energy was controlled by the kneading time of the planetary mixer, and the actual measured value was 70 Wh/kg. The temperature of the kneaded material was measured directly using a thermocouple, and the kneading temperature was 20-40° C. throughout kneading.

The particle L/D of the cellulose composite C obtained was 1.6. The storage modulus (G') was 2.9 Pa, the storage modulus in sodium bicarbonate aqueous solution was 1.7 Pa, the colloidal cellulose composite content was 76 mass %, the dynamic light scattering median diameter of the colloidal cellulose composites was 1.8 μm, the thixotropy was 2660, and the viscosity in sodium bicarbonate aqueous solution was 70 mPa·s. The results are shown in Table 1.

Example 4

Commercial DP pulp was chopped, then hydrolyzed for 15 minutes at 105° C. in 2.5 mol/L hydrochloric acid, then washed with water and filtered to produce wet cake cellulose having a solids fraction of 50 mass % (the average degree of polymerization was 220).

Next, the wet cake cellulose, commercial CMC-Na (viscosity of a 1% solution: 55 mPa·s, degree of etherification: 1.0-1.3), and commercial CMC-Ca (amount of water absorbed 6 g per gram) were prepared and introduced into a planetary mixer (manufactured by Shinagawa Kogyosho, 5DM-03-R, hook type stirring blades) to make an MCC/CMC-Na/CMC-Ca mass ratio of 84/13/3, and water was added to make a solids fraction of 45 mass %.

The contents were subsequently kneaded at 126 rpm, and a cellulose composite D was obtained. The kneading energy was controlled by the kneading time of the planetary mixer, and the actual measured value was 90 Wh/kg. The temperature of the kneaded material was measured directly using a thermocouple, and the kneading temperature was 20-60° C. throughout kneading.

The particle L/D of the cellulose composite D obtained was 1.6. The storage modulus (G') was 3.4 Pa, the storage modulus in sodium bicarbonate aqueous solution was 2.0 Pa, the colloidal cellulose composite content was 79 mass %, the dynamic light scattering median diameter of the colloidal cellulose composites was 2.8 μm, the thixotropy was 3120, and the viscosity in sodium bicarbonate aqueous solution was 100 mPa·s. The results are shown in Table 1.

Example 5

Commercial DP pulp was chopped, then hydrolyzed for 15 minutes at 105° C. in 2.5 mol/L hydrochloric acid, then washed with water and filtered to produce wet cake cellulose having a solids fraction of 50 mass % (the average degree of polymerization was 220).

Next, the wet cake cellulose, commercial CMC-Na (viscosity of a 1% solution: 55 mPa·s, degree of etherification: 1.0-1.3), and commercial CMC-Ca (amount of water absorbed 6 g per gram) were prepared and introduced into a planetary mixer (manufactured by Shinagawa Kogyosho, 5DM-03-R, hook type stirring blades) to make an MCC/CMC-Na/CMC-Ca mass ratio of 84/12/4, and water was added to make a solids fraction of 45 mass %.

The contents were subsequently kneaded at 126 rpm, and a cellulose composite E was obtained. The kneading energy was controlled by the kneading time of the planetary mixer, and the actual measured value was 100 Wh/kg. The temperature of the kneaded material was measured directly using a thermocouple, and the kneading temperature was 20-60° C. throughout kneading.

The particle L/D of the cellulose composite E obtained was 1.6. The storage modulus (G') was 3.6 Pa, the storage modulus in sodium bicarbonate aqueous solution was 2.1 Pa, the colloidal cellulose composite content was 82 mass %, the dynamic light scattering median diameter of the colloidal cellulose composites was 2.8 μm, the thixotropy was 3300, and the viscosity in sodium bicarbonate aqueous solution was 110 mPa·s. The results are shown in Table 1.

Example 6

Commercial DP pulp was chopped, then hydrolyzed for 15 minutes at 105° C. in 2.5 mol/L hydrochloric acid, then washed with water and filtered to produce wet cake cellulose having a solids fraction of 50 mass % (the average degree of polymerization was 220).

Next, the wet cake cellulose, commercial CMC-Na (viscosity of a 1% solution: 55 mPa·s, degree of etherification: 1.0-1.3), and commercial CMC-Ca (amount of water absorbed 6 g per gram) were prepared and introduced into a planetary mixer (manufactured by Shinagawa Kogyosho, 5DM-03-R, hook type stirring blades) to make an MCC/CMC-Na/CMC-Ca mass ratio of 84/8/8, and water was added to make a solids fraction of 45 mass %.

The contents were subsequently kneaded at 126 rpm, and a cellulose composite F was obtained. The kneading energy was controlled by the kneading time of the planetary mixer, and the actual measured value was 150 Wh/kg. The temperature of the kneaded material was measured directly using a thermocouple, and the kneading temperature was 40-70° C. throughout kneading.

The particle L/D of the cellulose composite F obtained was 1.6. The storage modulus (G') was 4.5 Pa, the storage modulus in sodium bicarbonate aqueous solution was 1.3 Pa, the colloidal cellulose composite content was 77 mass %, the dynamic light scattering median diameter of the colloidal cellulose composites was 3.0 μm, the thixotropy was 4130, and the viscosity in sodium bicarbonate aqueous solution was 40 mPa·s. The results are shown in Table 1.

Example 7

Commercial DP pulp was chopped, then hydrolyzed for 15 minutes at 105° C. in 2.5 mol/L hydrochloric acid, then washed with water and filtered to produce wet cake cellulose having a solids fraction of 50 mass % (the average degree of polymerization was 220).

Next, the wet cake cellulose, commercial CMC-Na (viscosity of a 1% solution: 55 mPa·s, degree of etherification:

1.0-1.3), and commercial CMC-Ca (amount of water absorbed 6 g per gram) were prepared and introduced into a planetary mixer (manufactured by Shinagawa Kogyosho, 5DM-03-R, hook type stirring blades) to make an MCC/CMC-Na/CMC-Ca mass ratio of 84/1/15, and water was added to make a solids fraction of 45 mass %.

The contents were subsequently kneaded at 126 rpm, and a cellulose composite G was obtained. The kneading energy was controlled by the kneading time of the planetary mixer, and the actual measured value was 170 Wh/kg. The temperature of the kneaded material was measured directly using a thermocouple, and the kneading temperature was 40-70° C. throughout kneading.

The particle L/D of the cellulose composite G obtained was 1.6. The storage modulus (G') was 0.8 Pa, the storage modulus in sodium bicarbonate aqueous solution was 0.4 Pa, the colloidal cellulose composite content was 60 mass %, the dynamic light scattering median diameter of the colloidal cellulose composites was 1.6 μm, the thixotropy was 730, and the viscosity in sodium bicarbonate aqueous solution was 12 mPa·s. The results are shown in Table 1.

Example 8

Commercial DP pulp was chopped, then hydrolyzed for 15 minutes at 105° C. in 2.5 mol/L hydrochloric acid, then washed with water and filtered to produce wet cake cellulose having a solids fraction of 50 mass % (the average degree of polymerization was 220).

Next, the wet cake cellulose, commercial CMC-Na (viscosity of a 1% solution: 55 mPa·s, degree of etherification: 1.0-1.3), and commercial CMC-Ca (amount of water absorbed 6 g per gram) were prepared and introduced into a planetary mixer (manufactured by Shinagawa Kogyosho, 5DM-03-R, hook type stirring blades) to make an MCC/CMC-Na/CMC-Ca mass ratio of 50/37.5/12.5, and water was added to make a solids fraction of 45 mass %.

The contents were subsequently kneaded at 126 rpm, and a cellulose composite H was obtained. The kneading energy was controlled by the kneading time of the planetary mixer, and the actual measured value was 70 Wh/kg. The temperature of the kneaded material was measured directly using a thermocouple, and the kneading temperature was 20-40° C. throughout kneading.

The particle L/D of the cellulose composite H obtained was 1.6. The storage modulus (G') was 0.9 Pa, the storage modulus in sodium bicarbonate aqueous solution was 0.5 Pa, the colloidal cellulose composite content was 63 mass %, the dynamic light scattering median diameter of the colloidal cellulose composites was 1.5 μm, the thixotropy was 825, and the viscosity in sodium bicarbonate aqueous solution was 50 mPa·s. The results are shown in Table 1.

Example 9

Commercial DP pulp was chopped, then hydrolyzed for 15 minutes at 105° C. in 2.5 mol/L hydrochloric acid, then washed with water and filtered to produce wet cake cellulose having a solids fraction of 50 mass % (the average degree of polymerization was 220).

Next, the wet cake cellulose, commercial CMC-Na (viscosity of a 1% solution: 55 mPa·s, degree of etherification: 1.0-1.3), and commercial CMC-Ca (amount of water absorbed 6 g per gram) were prepared and introduced into a planetary mixer (manufactured by Shinagawa Kogyosho, 5DM-03-R, hook type stirring blades) to make an MCC/CMC-Na/CMC-Ca mass ratio of 98/1.5/0.5, and water was added to make a solids fraction of 45 mass %.

The contents were subsequently kneaded at 126 rpm, and a cellulose composite I was obtained. The kneading energy was controlled by the kneading time of the planetary mixer, and the actual measured value was 120 Wh/kg. The temperature of the kneaded material was measured directly using a thermocouple, and the kneading temperature was 40-70° C. throughout kneading.

The particle L/D of the cellulose composite I obtained was 1.6. The storage modulus (G') was 0.7 Pa, the storage modulus in sodium bicarbonate aqueous solution was 0.4 Pa, the colloidal cellulose composite content was 51 mass %, the dynamic light scattering median diameter of the colloidal cellulose composites was 1.5 μm, the thixotropy was 660, and the viscosity in sodium bicarbonate aqueous solution was 14 mPa·s. The results are shown in Table 1.

Example 10

Commercial DP pulp was chopped, then hydrolyzed for 15 minutes at 105° C. in 2.5 mol/L hydrochloric acid, then washed with water and filtered to produce wet cake cellulose having a solids fraction of 50 mass % (the average degree of polymerization was 220).

Next, the wet cake cellulose, commercial CMC-Na (viscosity of a 1% solution: 55 mPa·s, degree of etherification: 1.0-1.3), and commercial hydroxyphosphoric acid-crosslinked starch (amount of water absorbed 3 g per gram) were prepared and introduced into a planetary mixer (manufactured by Shinagawa Kogyosho, 5DM-03-R, hook type stirring blades) to make an MCC/CMC-Na/hydroxyphosphoric acid-crosslinked starch mass ratio of 84/12/4, and water was added to make a solids fraction of 45 mass %.

The contents were subsequently kneaded at 126 rpm, and a cellulose composite J was obtained. The kneading energy was controlled by the kneading time of the planetary mixer, and the actual measured value was 80 Wh/kg. The temperature of the kneaded material was measured directly using a thermocouple, and the kneading temperature was 30-50° C. throughout kneading.

The particle L/D of the cellulose composite J obtained was 1.6. The storage modulus (G') was 3.0 Pa, the storage modulus in sodium bicarbonate aqueous solution was 1.8 Pa, the colloidal cellulose composite content was 80 mass %, the dynamic light scattering median diameter of the colloidal cellulose composites was 2.6 μm, the thixotropy was 2750, and the viscosity in sodium bicarbonate aqueous solution was 85 mPa·s. The results are shown in Table 1.

Example 11

Commercial DP pulp was chopped, then hydrolyzed for 15 minutes at 105° C. in 2.5 mol/L hydrochloric acid, then washed with water and filtered to produce wet cake cellulose having a solids fraction of 50 mass % (the average degree of polymerization was 220).

Next, the wet cake cellulose, commercial CMC-Na (viscosity of a 1% solution: 55 mPa·s, degree of etherification: 1.0-1.3), and commercial croscarmellose sodium (amount of water absorbed 6.5 g per gram) were prepared and introduced into a planetary mixer (manufactured by Shinagawa Kogyosho, 5DM-03-R, hook type stirring blades) to make an MCC/CMC-Na/croscarmellose sodium mass ratio of 84/12/4, and water was added to make a solids fraction of 45 mass %.

The contents were subsequently kneaded at 126 rpm, and a cellulose composite K was obtained. The kneading energy was controlled by the kneading time of the planetary mixer, and the actual measured value was 110 Wh/kg. The temperature of the kneaded material was measured directly using a thermocouple, and the kneading temperature was 20-70° C. throughout kneading.

The particle L/D of the cellulose composite K obtained was 1.6. The storage modulus (G') was 3.8 Pa, the storage modulus in sodium bicarbonate aqueous solution was 2.2 Pa, the colloidal cellulose composite content was 80 mass %, the dynamic light scattering median diameter of the colloidal cellulose composites was 2.8 μm, the thixotropy was 3500, and the viscosity in sodium bicarbonate aqueous solution was 120 mPa·s. The results are shown in Table 1.

Example 12

Commercial DP pulp was chopped, then hydrolyzed for 15 minutes at 105° C. in 2.5 mol/L hydrochloric acid, then washed with water and filtered to produce wet cake cellulose having a solids fraction of 50 mass % (the average degree of polymerization was 220).

Next, the wet cake cellulose, commercial CMC-Na (viscosity of a 1% solution: 55 mPa·s, degree of etherification: 1.0-1.3), and commercial calcium alginate (amount of water absorbed 3.2 g per gram) were prepared and introduced into a planetary mixer (manufactured by Shinagawa Kogyosho, 5DM-03-R, hook type stirring blades) to make an MCC/CMC-Na/calcium alginate mass ratio of 84/12/4, and water was added to make a solids fraction of 45 mass %.

The contents were subsequently kneaded at 126 rpm, and a cellulose composite L was obtained. The kneading energy was controlled by the kneading time of the planetary mixer, and the actual measured value was 80 Wh/kg. The temperature of the kneaded material was measured directly using a thermocouple, and the kneading temperature was 30-60° C. throughout kneading.

The particle L/D of the cellulose composite L obtained was 1.6. The storage modulus (G') was 3.1 Pa, the storage modulus in sodium bicarbonate aqueous solution was 1.8 Pa, the colloidal cellulose composite content was 76 mass %, the dynamic light scattering median diameter of the colloidal cellulose composites was 2.3 μm, the thixotropy was 2840, and the viscosity in sodium bicarbonate aqueous solution was 88 mPa·s. The results are shown in Table 1.

Example 13

Commercial DP pulp was chopped, then hydrolyzed for 15 minutes at 105° C. in 2.5 mol/L hydrochloric acid, then washed with water and filtered to produce wet cake cellulose having a solids fraction of 50 mass % (the average degree of polymerization was 220).

Next, the wet cake cellulose, commercial CMC-Na (viscosity of a 1% solution: 250 mPa·s, degree of etherification: 1.0-1.3), and commercial CMC-Ca (amount of water absorbed 6 g per gram) were prepared and introduced into a planetary mixer (manufactured by Shinagawa Kogyosho, 5DM-03-R, hook type stirring blades) to make an MCC/CMC-Na/CMC-Ca mass ratio of 84/12/4, and water was added to make a solids fraction of 45 mass %.

The contents were subsequently kneaded at 126 rpm, and a cellulose composite M was obtained. The kneading energy was controlled by the kneading time of the planetary mixer, and the actual measured value was 80 Wh/kg. The temperature of the kneaded material was measured directly using a thermocouple, and the kneading temperature was 20-40° C. throughout kneading.

The particle L/D of the cellulose composite M obtained was 1.6. The storage modulus (G') was 2.7 Pa, the storage modulus in sodium bicarbonate aqueous solution was 1.6 Pa, the colloidal cellulose composite content was 79 mass %, the dynamic light scattering median diameter of the colloidal cellulose composites was 2.5 μm, the thixotropy was 2475, and the viscosity in sodium bicarbonate aqueous solution was 65 mPa·s. The results are shown in Table 1.

Example 14

Commercial DP pulp was chopped, then hydrolyzed for 15 minutes at 105° C. in 2.5 mol/L hydrochloric acid, then washed with water and filtered to produce wet cake cellulose having a solids fraction of 50 mass % (the average degree of polymerization was 220).

Next, the wet cake cellulose, commercial CMC-Na (viscosity of a 2% solution: 11 mPa·s, degree of etherification: 0.7-0.8), and commercial CMC-Ca (amount of water absorbed 6 g per gram) were prepared and introduced into a planetary mixer (manufactured by Shinagawa Kogyosho, 5DM-03-R, hook type stirring blades) to make an MCC/CMC-Na/CMC-Ca mass ratio of 84/12/4, and water was added to make a solids fraction of 45 mass %.

The contents were subsequently kneaded at 126 rpm, and a cellulose composite N was obtained. The kneading energy was controlled by the kneading time of the planetary mixer, and the actual measured value was 90 Wh/kg. The temperature of the kneaded material was measured directly using a thermocouple, and the kneading temperature was 20-60° C. throughout kneading.

The particle L/D of the cellulose composite N obtained was 1.6. The storage modulus (G') was 3.3 Pa, the storage modulus in sodium bicarbonate aqueous solution was 1.9 Pa, the colloidal cellulose composite content was 77 mass %, the dynamic light scattering median diameter of the colloidal cellulose composites was 2.6 μm, the thixotropy was 3030, and the viscosity in sodium bicarbonate aqueous solution was 90 mPa·s. The results are shown in Table 1.

Example 15

Commercial DP pulp was chopped, then hydrolyzed for 15 minutes at 105° C. in 2.5 mol/L hydrochloric acid, then washed with water and filtered to produce wet cake cellulose having a solids fraction of 50 mass % (the average degree of polymerization was 220).

Next, the wet cake cellulose, commercial xanthan gum (manufactured by San-Ei Gen FFI, Inc., Vistop D-3000), and commercial CMC-Ca (amount of water absorbed 6 g per gram) were prepared and introduced into a planetary mixer (manufactured by Shinagawa Kogyosho, 5DM-03-R, hook type stirring blades) to make an MCC/xanthan gum/CMC-Ca mass ratio of 84/12/4, and water was added to make a solids fraction of 45 mass %.

The contents were subsequently kneaded at 126 rpm, and a cellulose composite O was obtained. The kneading energy was controlled by the kneading time of the planetary mixer, and the actual measured value was 60 Wh/kg. The temperature of the kneaded material was measured directly using a thermocouple, and the kneading temperature was 20-50° C. throughout kneading.

The particle L/D of the cellulose composite O obtained was 1.6. The storage modulus (G') was 1.5 Pa, the storage modulus in sodium bicarbonate aqueous solution was 0.9 Pa, the colloidal cellulose composite content was 61 mass %, the dynamic light scattering median diameter of the colloidal cellulose composites was 2.0 μm, the thixotropy was 1375, and the viscosity in sodium bicarbonate aqueous solution was 50 mPa·s. The results are shown in Table 1.

Comparative Example 1

After chopping commercial DP pulp by the same procedure as in the examples, the pulp was hydrolyzed for 15 minutes at 105° C. in 2.5 mol/L hydrochloric acid, then washed with water and filtered to produce wet cake cellulose having a solids fraction of 50 mass % (average degree of polymerization 220).

Next, the wet cake cellulose, CMC-Na (viscosity of 1% solution: 55 mPa·s, degree of etherification: 1.0-1.3), and commercial CMC-Ca (amount of water absorbed 6 g per gram) were prepared and introduced into a planetary mixer (manufactured by Shinagawa Kogyosho, 5DM-03-R, hook type stirring blades) to make an MCC/CMC-Na/CMC-Ca mass ratio of 84/15.6/0.4, and water was added to make a solids fraction of 45 mass %.

The contents were subsequently kneaded at 126 rpm, and a cellulose composite P was obtained. The kneading energy was controlled by the kneading time of the planetary mixer, and the actual measured value was 30 Wh/kg. The temperature of the kneaded material was measured directly using a thermocouple, and the kneading temperature was 20-30° C. throughout kneading.

The particle L/D of the cellulose composite P obtained was 1.6. The storage modulus (G') was 0.5 Pa, the storage modulus in sodium bicarbonate aqueous solution was 0.3 Pa, the colloidal cellulose composite content was 64 mass %, the dynamic light scattering median diameter of the colloidal cellulose composites was 0.9 μm, the thixotropy was 460, and the viscosity in sodium bicarbonate aqueous solution was 7 mPa·s. The results are shown in Table 1.

Comparative Example 2

Commercial DP pulp was chopped, then hydrolyzed for 15 minutes at 105° C. in 2.5 mol/L hydrochloric acid, then washed with water and filtered to produce wet cake cellulose having a solids fraction of 50 mass % (average degree of polymerization 220).

Next, the wet cake cellulose, CMC-Na (viscosity of 1% solution: 55 mPa·s, degree of etherification: 1.0-1.3), and commercial CMC-Ca (amount of water absorbed 6 g per gram) were prepared and introduced into a planetary mixer (manufactured by Shinagawa Kogyosho, 5DM-03-R, hook type stirring blades) to make an MCC/CMC-Na/CMC-Ca mass ratio of 83/1/16, and water was added to make a solids fraction of 45 mass %.

The contents were subsequently kneaded at 126 rpm, and a cellulose composite Q was obtained. The kneading energy was controlled by the kneading time of the planetary mixer, and the actual measured value was 190 Wh/kg. The temperature of the kneaded material was measured directly using a thermocouple, and the kneading temperature was 40-80° C. throughout kneading.

The particle L/D of the cellulose composite Q obtained was 1.6. The storage modulus (G') was 0.6 Pa, the storage modulus in sodium bicarbonate aqueous solution was 0.3 Pa, the colloidal cellulose composite content was 48 mass %, the dynamic light scattering median diameter of the colloidal cellulose composites was 0.6 μm, the thixotropy was 550, and the viscosity in sodium bicarbonate aqueous solution was 5 mPa·s. The results are shown in Table 1.

Comparative Example 3

Commercial DP pulp was chopped, then hydrolyzed for 15 minutes at 105° C. in 2.5 mol/L hydrochloric acid, then washed with water and filtered to produce wet cake cellulose having a solids fraction of 50 mass % (average degree of polymerization 220).

Next, the wet cake cellulose, CMC-Na (viscosity of 1% solution: 55 mPa·s, degree of etherification: 1.0-1.3), and commercial propylene glycol alginate (PGA hereinafter) (amount of water absorbed 3 g per gram) were prepared and introduced into a planetary mixer (manufactured by Shinagawa Kogyosho, 5DM-03-R, hook type stirring blades) to make an MCC/CMC-Na/PGA mass ratio of 84/12/4, and water was added to make a solids fraction of 45 mass %.

The contents were subsequently kneaded at 126 rpm, and a cellulose composite R was obtained. The kneading energy was controlled by the kneading time of the planetary mixer, and the actual measured value was 70 Wh/kg. The temperature of the kneaded material was measured directly using a thermocouple, and the kneading temperature was 20-40° C. throughout kneading.

The particle L/D of the cellulose composite R obtained was 1.6. The storage modulus (G') was 1.1 Pa, the storage modulus in sodium bicarbonate aqueous solution was 0.5 Pa, the colloidal cellulose composite content was 79 mass %, the dynamic light scattering median diameter of the colloidal cellulose composites was 2.1 μm, the thixotropy was 1000, and the viscosity in sodium bicarbonate aqueous solution was 20 mPa·s. The results are shown in Table 1.

Comparative Example 4

Commercial DP pulp was chopped, then hydrolyzed for 15 minutes at 105° C. in 2.5 mol/L hydrochloric acid, then washed with water and filtered to produce wet cake cellulose having a solids fraction of 50 mass % (average degree of polymerization 220).

Next, the wet cake cellulose, CMC-Na (viscosity of 1% solution: 55 mPa·s, degree of etherification: 1.0-1.3), and commercial gellan gum (manufactured by San-Ei Gen FFI, Inc., native gellan gum Kelcogel LT-100) (amount of water absorbed 24 g per gram) were prepared and introduced into a planetary mixer (manufactured by Shinagawa Kogyosho, 5DM-03-R, hook type stirring blades) to make an MCC/CMC-Na/gellan gum mass ratio of 84/12/4, and water was added to make a solids fraction of 45 mass %.

The contents were subsequently kneaded at 126 rpm, and a cellulose composite S was obtained. The kneading energy was controlled by the kneading time of the planetary mixer, and the actual measured value was 250 Wh/kg. The temperature of the kneaded material was measured directly using a thermocouple, and the kneading temperature was 50-90° C. throughout kneading.

The particle L/D of the cellulose composite S obtained was 1.6. The storage modulus (G') was 6.4 Pa, the storage modulus in sodium bicarbonate aqueous solution was 3.7 Pa, the colloidal cellulose composite content was 61 mass %, the dynamic light scattering median diameter of the colloidal cellulose composites was 1.7 μm, the thixotropy was 5900, and the viscosity in sodium bicarbonate aqueous solution was 210 mPa·s. The results are shown in Table 1.

Comparative Example 5

Commercial DP pulp was chopped, then hydrolyzed for 15 minutes at 105° C. in 2.5 mol/L hydrochloric acid, then washed with water and filtered to produce wet cake cellulose having a solids fraction of 50 mass % (average degree of polymerization 220).

Next, the wet cake cellulose, CMC-Na (viscosity of 1% solution: 55 mPa·s, degree of etherification: 1.0-1.3), and commercial CMC-Ca (amount of water absorbed 6 g per gram) were prepared and introduced into a planetary mixer (manufactured by Shinagawa Kogyosho, 5DM-03-R, hook type stirring blades) to make an MCC/CMC-Na/CMC-Ca mass ratio of 49/38/13, and water was added to make a solids fraction of 45 mass %.

The contents were subsequently kneaded at 126 rpm, and a cellulose composite T was obtained. The kneading energy was controlled by the kneading time of the planetary mixer, and the actual measured value was 60 Wh/kg. The temperature of the kneaded material was measured directly using a thermocouple, and the kneading temperature was 20-40° C. throughout kneading.

The particle L/D of the cellulose composite T obtained was 1.6. The storage modulus (G') was 0.7 Pa, the storage modulus in sodium bicarbonate aqueous solution was 0.3 Pa, the colloidal cellulose composite content was 62 mass %, the dynamic light scattering median diameter of the colloidal cellulose composites was 1.2 µm, the thixotropy was 710, and the viscosity in sodium bicarbonate aqueous solution was 7 mPa·s. The results are shown in Table 1.

Comparative Example 6

Commercial DP pulp was chopped, then hydrolyzed for 15 minutes at 105° C. in 2.5 mol/L hydrochloric acid, then washed with water and filtered to produce wet cake cellulose having a solids fraction of 50 mass % (average degree of polymerization 220).

Next, the wet cake cellulose, CMC-Na (viscosity of 1% solution: 55 mPa·s, degree of etherification: 1.0-1.3), and commercial CMC-Ca (amount of water absorbed 6 g per gram) were prepared and introduced into a planetary mixer (manufactured by Shinagawa Kogyosho, 5DM-03-R, hook type stirring blades) to make an MCC/CMC-Na/CMC-Ca mass ratio of 99.5/0.38/0.13, and water was added to make a solids fraction of 45 mass %.

The contents were subsequently kneaded at 126 rpm, and a cellulose composite U was obtained. The kneading energy was controlled by the kneading time of the planetary mixer, and the actual measured value was 100 Wh/kg. The temperature of the kneaded material was measured directly using a thermocouple, and the kneading temperature was 40-80° C. throughout kneading.

The particle L/D of the cellulose composite U obtained was 1.6. The storage modulus (G') was 0.5 Pa, the storage modulus in sodium bicarbonate aqueous solution was 0.2 Pa, the colloidal cellulose composite content was 45 mass %, the dynamic light scattering median diameter of the colloidal cellulose composites was 1.3 µm, the thixotropy was 460, and the viscosity in sodium bicarbonate aqueous solution was 3 mPa·s. The results are shown in Table 1.

Comparative Example 7

Hydrolysis of cellulose was carried out using commercial KP pulp. Next, wet cake cellulose (average degree of polymerization 220), commercial CMC-Na (viscosity of 2% solution: 620 mPa·s, degree of etherification: 1.0-1.3) as component A, and commercial CMC-Na (viscosity of 2% solution: 25 mPa·s, degree of etherification: 1.0-1.3) as component B were prepared and introduced to make a MCC/CMC-Na (component A+component B) mass ratio of 90/10 (composition of CMC-Na: component A/component B=40/60). Water was added to make a solids fraction of 45 mass %, kneading was conducted in the same way as in Example 1, and a cellulose composite V was obtained. The kneading energy was controlled by the kneading time of the planetary mixer, and the actual measured value was 100 Wh/kg. The kneading temperature was adjusted by jacket cooling. The temperature of the kneaded material was measured directly using a thermocouple, and the kneading temperature was 20-60° C. throughout kneading.

The particle L/D of the cellulose composite V obtained was 1.6. The storage modulus (G') was 2.5 Pa, the storage modulus in sodium bicarbonate aqueous solution was 0.1 Pa, the colloidal cellulose composite content was 72 mass %, the dynamic light scattering median diameter of the colloidal cellulose composites was 1.2 µm, the thixotropy was 2300, and the viscosity in sodium bicarbonate aqueous solution was 3 mPa·s. The results are shown in Table 1.

<High Ionic Concentration Concentrated Liquid Food>

High ionic concentration concentrated liquid foods were produced by the following procedure using the cellulose composites A-V obtained in the above examples and comparative examples, and evaluated.

Ion-exchanged water that had been warmed to 70° C. was added to 46.0 g of soybean oil and 3.45 g of the emulsifier lecithin to make 1852.29 g. Mixing and dispersion were conducted subsequently by a TK homomixer (Model Mark II, manufactured by Tokushu Kika Kogyo Co., Ltd., 7000 rpm×3 minutes at 60° C.). A premix of 28.75 g of casein Na, 86.25 g of soybean protein, and 299.0 g of dextrin was then added and stirred by a propeller (700 rpm×20 seconds). Then, 8.40 g of sodium bicarbonate, 9.22 g of dipotassium hydrogen phosphate, 6.88 g of calcium carbonate, 4.00 g of magnesium carbonate, 0.15 g of ammonium citrate, and 0.46 g of dry yeast (zinc) as mineral components and 4.60 g of cellulose composite were added to make a liquid food with a total amount of 2300 g. Furthermore, the total ionic strength of the sodium bicarbonate, dipotassium hydrogen phosphate, calcium carbonate, magnesium carbonate, and ammonium citrate in this liquid food was calculated to be 0.65.

After mixing and dispersing by a TK homomixer (7000 rpm×1 minute at 70° C.), homogenization treatment (50 MPa) was carried out by a piston-type homogenizer. Two hundred fifty milliliter heat-resistant bottles were filled, and a high ionic concentration concentrated liquid food was obtained. Heat sterilization (121° C., 15 minutes) was performed thereafter. After cooling for one hour by tap water, the product was shaken by gently inverting the container 10 times. The containers were stored standing for one month in a 40° C. atmosphere, and the appearance was examined visually. The evaluation methods were as follows, and the results obtained are shown in Table 1.

<Suspension Stability: Examination of Appearance of Food or Beverage>

The following four parameters were established as criteria, and the appearance of various beverages (refer to the following examples and comparative examples for the production methods) was assessed visually.

(Separation) Separation was evaluated according to the following evaluation criteria based on the volume of the pale layer at the top of the beverage in the heat-resistant bottle.

⊙ (excellent): no separation

○ (good): less than 10% separation

Δ (fair): less than 30% separation x (poor): 30% or more separation (Precipitation) Precipitation was evaluated according to the following evaluation criteria based on the amount of sediment at the bottom of the beverage in the heat-resistant bottle.
⊙ (excellent): no precipitation
○ (good): partial thin precipitation
Δ (fair): thin precipitation over surface
x (poor): overall thick precipitation (Aggregation) Aggregation was evaluated according to the following evaluation criteria based on the amount of nonuniform parts in the entire beverage in the heat-resistant bottle.

⊙ (excellent): uniform
○ (good): slight partial nonuniformity
Δ (fair): partial nonuniformity
x (poor): overall nonuniformity (Texture) Texture was evaluated according to the following evaluation criteria.
⊙ (excellent): goes lightly down the throat, proper body
○ (good): somewhat pasty feeling in going down throat
Δ (fair): heavy going down throat and very pasty feeling
x (poor): goes down throat well, but feels watery; or, heavy going down throat and strongly pasty feeling

TABLE 1

| | | | Composition (mass %) | | | | | | | |
|---|---|---|---|---|---|---|---|---|---|---|
| | | | Anionic polysaccharide (mass %) | | | Water-absorbent particles (mass %) | | | | |
| | Cellulose composite | Cellulose (mass %) | CMC-Na | Xanthan gum | CMC-Ca | Hydroxyphosphoric acid-crosslinked starch | Croscarmellose sodium | PGA | Gellan gum | Calcium alginate |
| Example 1 | A | 84 | 15.5 | — | 0.5 | — | — | — | — | — |
| Example 2 | B | 84 | 14 | — | 2.0 | — | — | — | — | — |
| Example 3 | C | 84 | 13.5 | — | 2.5 | — | — | — | — | — |
| Example 4 | D | 84 | 13 | — | 3.0 | — | — | — | — | — |
| Example 5 | E | 84 | 12 | — | 4.0 | — | — | — | — | — |
| Example 6 | F | 84 | 8 | — | 8.0 | — | — | — | — | — |
| Example 7 | G | 84 | 1 | — | 15 | — | — | — | — | — |
| Example 8 | H | 50 | 37.5 | — | 12.5 | — | — | — | — | — |
| Example 9 | I | 98 | 1.5 | — | 0.5 | — | — | — | — | — |
| Example 10 | J | 84 | 12 | — | — | 4 | — | — | — | — |
| Example 11 | K | 84 | 12 | — | — | — | 4 | — | — | — |
| Example 12 | L | 84 | 12 | — | — | — | — | — | — | 4 |
| Example 13 | M | 84 | 12 | — | 4 | — | — | — | — | — |
| Example 14 | N | 84 | 12 | — | 4 | — | — | — | — | — |
| Example 15 | O | 84 | — | 12 | 4 | — | — | — | — | — |
| Comparative example 1 | P | 84 | 15.6 | — | 0.4 | — | — | — | — | — |
| Comparative example 2 | Q | 83 | 1 | — | 16 | — | — | — | — | — |
| Comparative example 3 | R | 84 | 12 | — | — | — | — | 4 | — | — |
| Comparative example 4 | S | 84 | 12 | — | — | — | — | — | 4 | — |
| Comparative example 5 | T | 49 | 38 | — | 13 | — | — | — | — | — |
| Comparative example 6 | U | 99.5 | 0.38 | — | 0.13 | — | — | — | — | — |
| Comparative example 7 | V | 90 | 10 | — | — | — | — | — | — | — |

| | Properties of water-absorbent material (mL/g) | Configuration of CMC-Na | | | | |
|---|---|---|---|---|---|---|
| | | | | Compositing conditions | | |
| | Water absorbency (mL/g) | Viscosity (mPa·s) | Degree of etherification (—) | Solids fraction (mass %) | Kneading energy (Wh/kg) | Kneading temperature (° C.) |
| Example 1 | 6.0 | 55 | 1.0-1.3 | 45 | 40 | 20-40 |
| Example 2 | 6.0 | 55 | 1.0-1.3 | 45 | 50 | 20-40 |
| Example 3 | 6.0 | 55 | 1.0-1.3 | 45 | 70 | 20-40 |
| Example 4 | 6.0 | 55 | 1.0-1.3 | 45 | 90 | 20-60 |
| Example 5 | 6.0 | 55 | 1.0-1.3 | 45 | 100 | 20-60 |
| Example 6 | 6.0 | 55 | 1.0-1.3 | 45 | 150 | 40-70 |
| Example 7 | 6.0 | 55 | 1.0-1.3 | 45 | 170 | 40-70 |
| Example 8 | 6.0 | 55 | 1.0-1.3 | 45 | 70 | 20-40 |
| Example 9 | 6.0 | 55 | 1.0-1.3 | 45 | 120 | 40-70 |
| Example 10 | 3.0 | 55 | 1.0-1.3 | 45 | 80 | 30-50 |
| Example 11 | 6.5 | 55 | 1.0-1.3 | 45 | 110 | 20-70 |
| Example 12 | 3.2 | 55 | 1.0-1.3 | 45 | 80 | 30-60 |
| Example 13 | 6.0 | 250 | 1.0-1.3 | 45 | 80 | 20-40 |
| Example 14 | 6.0 | 11 | 0.7-0.8 | 45 | 90 | 20-60 |
| Example 15 | 6.0 | — | — | 45 | 60 | 20-50 |

TABLE 1-continued

| | | | | | | |
|---|---|---|---|---|---|---|
| Comparative example 1 | 6.0 | 55 | 1.0-1.3 | 45 | 30 | 20-30 |
| Comparative example 2 | 6.0 | 55 | 1.0-1.3 | 45 | 190 | 40-80 |
| Comparative example 3 | 3.0 | 55 | 1.0-1.3 | 45 | 70 | 20-40 |
| Comparative example 4 | 24.0 | 55 | 1.0-1.3 | 45 | 250 | 50-90 |
| Comparative example 5 | 6.0 | 55 | 1.0-1.3 | 45 | 60 | 20-40 |
| Comparative example 6 | 6.0 | 55 | 1.0-1.3 | 45 | 100 | 40-80 |
| Comparative example 7 | — | 620, 25 (A, B) | 1.0-1.3 (both A and B) | 45 | 100 | 20-60 |

| | Basic properties of composite | | | | | | |
|---|---|---|---|---|---|---|---|
| | Average degree of polymerization of cellulose (—) | Particle L/D of cellulose (—) | G' of composite (Pa) | G' in sodium bicarbonate aqueous solution (Pa) | Colloidal cellulose composite content (mass %) | Dynamic light scattering median diameter (μm) | Thixotropy (—) | Viscosity in sodium bicarbonate aqueous solution (mPa · s) |
| Example 1 | 220 | 1.6 | 0.7 | 0.4 | 68 | 1.5 | 640 | 10 |
| Example 2 | 220 | 1.6 | 1.7 | 1.0 | 73 | 1.7 | 1560 | 30 |
| Example 3 | 220 | 1.6 | 2.9 | 1.7 | 76 | 1.8 | 2660 | 70 |
| Example 4 | 220 | 1.6 | 3.4 | 2.0 | 79 | 2.8 | 3120 | 100 |
| Example 5 | 220 | 1.6 | 3.6 | 2.1 | 82 | 2.8 | 3300 | 110 |
| Example 6 | 220 | 1.6 | 4.5 | 1.3 | 77 | 3.0 | 4130 | 40 |
| Example 7 | 220 | 1.6 | 0.8 | 0.4 | 60 | 1.6 | 730 | 12 |
| Example 8 | 220 | 1.6 | 0.9 | 0.5 | 63 | 1.5 | 825 | 50 |
| Example 9 | 220 | 1.6 | 0.7 | 0.4 | 51 | 1.5 | 660 | 14 |
| Example 10 | 220 | 1.6 | 3.0 | 1.8 | 80 | 2.6 | 2750 | 85 |
| Example 11 | 220 | 1.6 | 3.8 | 2.2 | 80 | 2.8 | 3500 | 120 |
| Example 12 | 220 | 1.6 | 3.1 | 1.8 | 76 | 2.3 | 2840 | 88 |
| Example 13 | 220 | 1.6 | 2.7 | 1.6 | 79 | 2.5 | 2475 | 65 |
| Example 14 | 220 | 1.6 | 3.3 | 1.9 | 77 | 2.6 | 3030 | 90 |
| Example 15 | 220 | 1.6 | 1.5 | 0.9 | 61 | 2.0 | 1375 | 50 |
| Comparative example 1 | 220 | 1.6 | 0.5 | 0.3 | 64 | 0.9 | 460 | 7 |
| Comparative example 2 | 220 | 1.6 | 0.6 | 0.3 | 48 | 0.6 | 550 | 5 |
| Comparative example 3 | 220 | 1.6 | 1.1 | 0.5 | 79 | 2.1 | 1000 | 20 |
| Comparative example 4 | 220 | 1.6 | 6.4 | 3.7 | 61 | 1.7 | 5900 | 210 |
| Comparative example 5 | 220 | 1.6 | 0.7 | 0.3 | 62 | 1.2 | 710 | 7 |
| Comparative example 6 | 220 | 1.6 | 0.5 | 0.2 | 45 | 1.3 | 460 | 3 |
| Comparative example 7 | 220 | 1.6 | 2.5 | 0.1 | 72 | 1.2 | 2300 | 3 |

| | Results of evaluation of high ionic strength concentrated liquid food | | | |
|---|---|---|---|---|
| | Precipitation | Aggregation | Separation | Texture (taste) |
| Example 1 | Δ | ⊙ | ⊙ | ○ |
| Example 2 | Δ | ⊙ | ⊙ | ○ |
| Example 3 | ○ | ⊙ | ⊙ | ⊙ |
| Example 4 | ○ | ⊙ | ⊙ | ⊙ |
| Example 5 | ⊙ | ⊙ | ⊙ | ⊙ |
| Example 6 | Δ | ⊙ | ⊙ | ○ |
| Example 7 | Δ | ○ | ⊙ | ○ |
| Example 8 | Δ | ⊙ | ⊙ | Δ |
| Example 9 | Δ | Δ | ○ | ○ |
| Example 10 | ○ | ⊙ | ⊙ | ⊙ |
| Example 11 | ⊙ | ⊙ | ⊙ | ⊙ |
| Example 12 | ○ | ⊙ | ⊙ | ⊙ |
| Example 13 | ○ | ⊙ | ⊙ | ⊙ |
| Example 14 | ○ | ⊙ | ⊙ | ⊙ |
| Example 15 | Δ | ⊙ | ⊙ | Δ |
| Comparative example 1 | X | ○ | ○ | Δ |
| Comparative example 2 | X | Δ | Δ | Δ |
| Comparative example 3 | Δ | Δ | Δ | X |

TABLE 1-continued

| | | | | |
|---|---|---|---|---|
| Comparative example 4 | ⊙ | ⊙ | ⊙ | X |
| Comparative example 5 | X | ○ | ○ | Δ |
| Comparative example 6 | X | X | X | X |
| Comparative example 7 | X | X | X | X |

<Coffee Beverage>

Coffee beverages were produced by the following procedure using cellulose composite E obtained in the above Example 5 and cellulose composite R obtained in Comparative Example 3, and evaluated.

Two hundred fifty grams of coffee powder (manufactured by Key Coffee Co., Ltd., product name "Premium Blend") was soaked by adding 60° C. water to make a total of 1000 g. After returning to normal temperature, the mixture was filtered by cotton flannel cloth, and a coffee extract was produced. The Brix of this extract was measured using a saccharimeter (manufactured by Atago Co., Ltd., product name "PAL-1"). As a result, the Brix was 4.0.

Next, 13.0 parts by mass of milk, 5.0 parts by mass of granulated sugar, 0.03 part by mass of emulsifier (manufactured by Mitsubishi Kagaku Foods Corporation, product name "Sucrose Fatty Acid Ester P-1670"), 0.60 part by mass of sodium bicarbonate (manufactured by Wako Pure Chemicals Co., Ltd., guaranteed grade), and 0.035 part by mass each of cellulose composite E or R (calculated for dry product) were added to 64.5 parts by mass of this coffee extract, and a coffee beverage was made by adding pure water to make a total of 100 parts by mass. Furthermore, since the ionic strength of an aqueous solution containing 6 g of sodium bicarbonate in one liter of water is 0.214, the ionic strength of the sodium carbonate contained in this coffee beverage corresponds to at least that value or higher.

The coffee beverage was placed in a 2 L stainless steel container and stirred by propeller (300 rpm, 10 minutes) at 80° C. The dispersion was then homogenized (20 MPa) by a piston-type homogenizer (manufactured by APV, product name "Manton-Gaulin homogenizer"). The homogenized product was subjected to UHT heat sterilization (140° C., 60 seconds), and 200 mL glass heat-resistant bottles were filled, stoppered, and cooled for one hour by tap water. After shaking by gently inverting the containers ten times, the bottles were allowed to stand for 28 days in a 60° C. atmosphere, and the appearance was examined visually. The evaluation methods were as follows.

<Suspension Stability: Examination of Appearance of Food or Beverage>

The following four parameters were established as criteria, and the appearance of each coffee beverage was assessed visually.

(Separation) Separation was evaluated according to the following evaluation criteria based on the volume of the pale layer at the top of the beverage in the heat-resistant bottle.

⊙ (excellent): no separation
○ (good): less than 10% separation
Δ (fair): less than 30% separation
x (poor): 30% or more separation (Precipitation) Precipitation was evaluated according to the following evaluation criteria based on the amount of sediment at the bottom of the beverage in the heat-resistant bottle.

⊙ (excellent): no precipitation
○ (good): partial thin precipitation
Δ (fair): thin precipitation over surface
x (poor): overall thick precipitation (Aggregation) Aggregation was evaluated according to the following evaluation criteria based on the amount of nonuniform parts in the entire beverage in the heat-resistant bottle.

⊙ (excellent): uniform
○ (good): slight partial nonuniformity
Δ (fair): partial nonuniformity
x (poor): overall nonuniformity (Oil ring) The oil ring was evaluated according to the following evaluation criteria based on the amount of ring-shaped oily solid confirmed along the walls of the bottle in the upper part of the beverage in the heat-resistant bottle.

⊙ (excellent): none
○ (good): slight partial development
Δ (fair): incomplete ring development
x (poor): complete ring development The above results for the coffee beverage blended with the cellulose composite E of Example 5 were separation ⊙, precipitation ⊙, aggregation ⊙, oil ring ⊙. In contrast, the beverage blended with the cellulose composite R of Comparative Example 3 was separation x, precipitation x, aggregation x, oil ring x. These results showed that the cellulose composite of this application has good dispersion and therefore exhibits high suspension stability even in systems containing neutral salts in which the amount of cellulose composite added is limited to a trace.

INDUSTRIAL APPLICABILITY

The cellulose composite of the present invention, when added to high ionic strength foods and beverages, can suppress the occurrence of separation, aggregation, and precipitation of components and exert suspension stabilization. In addition, since it has excellent suspension stability, the cellulose composite of the present invention is useful in beverages in which ordinary components of cocoa, coffee, black tea, milk or the like are blended. Moreover, in addition to these beverages, the cellulose composite of the present invention is useful because it presents excellent suspension stability even in foods and beverages that contain water-insoluble components such as functional food materials.

The invention claimed is:

1. A cellulose composite comprising:
cellulose,
an anionic polysaccharide not having a chemically crosslinked structure, and
0.5 to 15 mass % of water-absorbent particles comprising a compound having a chemically crosslinked structure, wherein the compound having the chemically crosslinked structure is carboxymethyl cellulose calcium having a degree of substitution of 0.5 to 2.0, wherein the water-absorbent particles have a saturated water absorption of 3 mL/g or higher,
wherein the cellulose composite has a viscosity of 10 mPa·s or higher when 1 mass % of the cellulose composite is dispersed in an aqueous solution in which 0.45 g of sodium bicarbonate is dissolved in 100 mL of pure water.

2. The cellulose composite of claim 1 wherein the anionic polysaccharide not having a chemically crosslinked structure is selected from the group consisting of carboxymethyl cellulose sodium and xanthan gum.

3. The cellulose composite of claim 1 wherein the anionic polysaccharide not having a chemically crosslinked structure is carboxymethyl cellulose sodium.

4. The cellulose composite of claim 1 wherein a blend ratio of the cellulose/the anionic polysaccharide not having a chemically crosslinked structure is 50-99 parts by mass/ 1-50 parts by mass.

5. A method for producing the cellulose composite of claim 1 comprising:
  compositing the cellulose, the anionic polysaccharide not having a chemically crosslinked structure, and the water-absorbent particles comprising the compound having a chemically crosslinked structure.

6. A food comprising the cellulose composite of claim 1.

7. An industrial product comprising the cellulose composite of claim 1.

8. A pharmaceutical comprising the cellulose composite of claim 1.

9. A coffee beverage comprising the cellulose composite of claim 1.

* * * * *